US012565535B2

(12) United States Patent
Priceman et al.

(10) Patent No.: US 12,565,535 B2
(45) Date of Patent: *Mar. 3, 2026

(54) CHIMERIC ANTIGEN RECEPTORS TARGETED TO PSCA

(71) Applicant: City of Hope, Duarte, CA (US)

(72) Inventors: Saul J. Priceman, Valley Village, CA (US); Christine E. Brown, Duarte, CA (US); Stephen J. Forman, Duarte, CA (US)

(73) Assignee: City of Hope, Duarte, CA (US)

( * ) Notice: Subject to any disclaimer, the term of this patent is extended or adjusted under 35 U.S.C. 154(b) by 528 days.

This patent is subject to a terminal disclaimer.

(21) Appl. No.: 17/820,440

(22) Filed: Aug. 17, 2022

(65) Prior Publication Data

US 2023/0348617 A1      Nov. 2, 2023

Related U.S. Application Data

(63) Continuation of application No. 15/766,674, filed as application No. PCT/US2016/055761 on Oct. 6, 2016, now Pat. No. 11,466,097.

(Continued)

(51) Int. Cl.

| | |
|---|---|
| *A61P 35/00* | (2006.01) |
| *A61K 35/17* | (2015.01) |
| *A61K 40/11* | (2025.01) |
| *A61K 40/31* | (2025.01) |
| *A61K 40/42* | (2025.01) |
| *A61K 48/00* | (2006.01) |
| *A61P 1/18* | (2006.01) |
| *A61P 19/08* | (2006.01) |
| *A61P 35/04* | (2006.01) |
| *C07H 21/00* | (2006.01) |
| *C07H 21/04* | (2006.01) |
| *C07K 14/705* | (2006.01) |
| *C07K 14/725* | (2006.01) |
| *C07K 14/73* | (2006.01) |
| *C07K 16/30* | (2006.01) |
| *C12N 5/00* | (2006.01) |
| *C12N 5/07* | (2010.01) |
| *C12N 5/071* | (2010.01) |
| *C12N 5/078* | (2010.01) |
| *C12N 5/0783* | (2010.01) |
| *C12N 5/10* | (2006.01) |
| *C12N 15/00* | (2006.01) |
| *C12N 15/09* | (2006.01) |
| *C12N 15/10* | (2006.01) |
| *C12N 15/11* | (2006.01) |
| *C12N 15/62* | (2006.01) |
| *C12N 15/63* | (2006.01) |
| *C12N 15/70* | (2006.01) |

(Continued)

(52) U.S. Cl.
CPC .......... *C07K 16/3069* (2013.01); *A61K 35/17* (2013.01); *A61K 40/11* (2025.01); *A61K 40/31* (2025.01); *A61K 40/4274* (2025.01); *A61K 48/00* (2013.01); *A61P 1/18* (2018.01); *A61P 19/08* (2018.01); *A61P 35/00* (2018.01); *A61P 35/04* (2018.01); *C07H 21/00* (2013.01); *C07H 21/04* (2013.01); *C07K 14/7051* (2013.01); *C07K 14/70514* (2013.01); *C07K 14/70517* (2013.01); *C07K 14/70521* (2013.01); *C12N 5/00* (2013.01); *C12N 5/06* (2013.01); *C12N 5/0602* (2013.01); *C12N 5/0634* (2013.01); *C12N 5/0636* (2013.01); *C12N 5/10* (2013.01); *C12N 15/00* (2013.01); *C12N 15/09* (2013.01); *C12N 15/10* (2013.01); *C12N 15/11* (2013.01); *C12N 15/62* (2013.01); *C12N 15/63* (2013.01); *C12N 15/70* (2013.01); *C12N 15/74* (2013.01); *C12N 15/79* (2013.01); *C12N 15/85* (2013.01); *A61K 2239/31* (2023.05); *A61K 2239/38* (2023.05); *C07H 19/00* (2013.01); *C07H 19/06* (2013.01); *C07H 19/16* (2013.01); *C07K 2317/24* (2013.01); *C07K 2317/53* (2013.01); *C07K 2317/622* (2013.01); *C07K 2317/73* (2013.01); *C07K 2317/76* (2013.01); *C07K 2319/02* (2013.01); *C07K 2319/03* (2013.01); *C07K 2319/33* (2013.01); *C12N 15/8509* (2013.01); *C12N 2015/8518* (2013.01); *C12N 2015/8572* (2013.01)

(58) Field of Classification Search
None
See application file for complete search history.

(56) References Cited

U.S. PATENT DOCUMENTS 11,466,097 B2      10/2022    Priceman et al.
2014/0090309 A1*    4/2014    Dumm ............... C01B 21/0722
                                                      51/307

(Continued)

FOREIGN PATENT DOCUMENTS

RU              2381234        2/2010
WO      WO 2005/000898        1/2005

(Continued)

OTHER PUBLICATIONS

Han et al., Journal of Urology, Mar. 1, 2004;171(3):1117-21. (Year: 2004).*

(Continued)

*Primary Examiner* — Zachary S Skelding
(74) *Attorney, Agent, or Firm* — Fish & Richardson P.C.

(57) ABSTRACT

Chimeric transmembrane immunoreceptors (CAR) targeted to PSCA are described.

19 Claims, 23 Drawing Sheets

Specification includes a Sequence Listing.

Related U.S. Application Data

(60) Provisional application No. 62/238,062, filed on Oct. 6, 2015.

(51) Int. Cl.

| | |
|---|---|
| *C12N 15/74* | (2006.01) |
| *C12N 15/79* | (2006.01) |
| *C12N 15/85* | (2006.01) |
| *C07H 19/00* | (2006.01) |
| *C07H 19/06* | (2006.01) |
| *C07H 19/16* | (2006.01) |

(56) References Cited

U.S. PATENT DOCUMENTS

| | | | |
|---|---|---|---|
| 2014/0356398 A1* | 12/2014 | Riddell | A61K 40/4221 |
| | | | 424/277.1 |
| 2015/0139943 A1 | 5/2015 | Campana et al. | |
| 2020/0308300 A1 | 10/2020 | Priceman et al. | |

FOREIGN PATENT DOCUMENTS

| | | | |
|---|---|---|---|
| WO | WO 2009/032949 | 3/2009 | |
| WO | WO 2012/079000 | 6/2012 | |
| WO | WO 2014/031687 | 2/2014 | |
| WO | WO 2014/144622 | 9/2014 | |
| WO | WO 2015/066551 | 5/2015 | |
| WO | WO 2015/105522 | 7/2015 | |
| WO | WO 2015/123527 | 8/2015 | |
| WO | WO 2015/157399 | 10/2015 | |
| WO | WO-2016138034 A1 * | 9/2016 | G01N 33/53 |
| WO | WO 2017/027325 | 2/2017 | |

OTHER PUBLICATIONS

Zhigang et al., World J Surg Oncol. May 10, 2004;2:13, pp. 1-7. (Year: 2004).*

Martin et al., Oncology Reports 31: 262-272, 2014. (Year: 2014).*

Abate-Daga et al., "Supplemental Information for: 'A novel chimeric antigen receptor against prostate stem cell antigen mediates tumor destruction in a humanized mouse model of pancreatic cancer,'" Human Gene Therapy, Dec. 2014, 25(12):1-4.

Leyton et al., "Engineered humanized diabodies for microPET imaging of prostate stem cell antigen-expressing tumors," Protein Engineering, Design & Selection, Mar. 2009, 22(3):209-216.

Abate-Daga et al., "A novel chimeric antigen receptor against prostate stem cell antigen mediates tumor destruction in a humanized mouse model of pancreatic cancer," Hum Gene Ther., Dec. 2014, 25(12):1003-1012.

Abate-Daga et al., "Pancreatic cancer: Hurdles in the engineering of CAR-based immunotherapies," Oncoimmunology, Jun. 18, 2014, 3:e29194-1-e29194-3.

Ahmed et al., "HER2-specific T cells target primary glioblastoma stem cells and induce regression of autologous experimental tumors," Clin Cancer Res, Jan. 15, 2010, 16(2):474-485.

Bedouelle et al., "Diversity and junction residues as hotspots of binding energy in an antibody neutralizing the dengue virus," FEBS J., Jan. 2006, 273(1):34-46.

Brown et al., "Tolerance of single, but not multiple, amino acid replacements in antibody VH CDR 2: a means of minimizing B cell wastage from somatic hypermutation?," J Immunol., May 1, 1996, 156(9):3285-3291.

Brown et al., "Stem-like tumor-initiating cells isolated from IL13Rα2 expressing gliomas are targeted and killed by IL13-zetakine-redirected T Cells," Clin Cancer Res., Apr. 15, 2012, 18(8):2199-209.

Brown et al., "Tumor-derived chemokine MCP-1/CCL2 is sufficient for mediating tumor tropism of adoptively transferred T cells," J Immunol., 2007, 179(5):3332-3341.

Cartellieri et al., "Chimeric antigen receptor-engineered T cells for immunotherapy of cancer," J Biomed Biotechnol, May 5, 2010, 2010, 21(4):427-413.

Cartellieri et al., "A Novel Ex Vivo Isolation and Expansion Procedure for Chimeric Antigen Receptor Engrafted Human T Cells," PLOS ONE, Apr. 2014, 9(4):e93745.

Chow et al., "T Cells Redirected to EphA2 for the Immunotherapy of Glioblastoma," Mol Ther., 2013, 21(3):629-637.

Colman "Effects of amino acid sequence changes on antibody-antigen interactions," Research in Immunology, Jan. 1994, 145:33-36.

Diamond et al., "Somatic mutation of the T15 heavy chain gives rise to an antibody with autoantibody specificity," Proc Natl Acad Sci USA., 1984, 81:5841-5844.

Dotti et al., "Design and development of therapies using chimeric antigen receptor-expressing T cells," Immunological Reviews, Jan. 2014, 257(1):107-126.

Edelman et al., "The covalent structure of an entire gammaG immunoglobulin molecule," Proc Natl Acad Sci USA, May 1969, 63(1):78-85.

European Search Report in European Application No. 20170726.2, dated Oct. 5, 2020, 20 pages.

Feldmann et al., "Novel Humanized and Highly Efficient Bispecific Antibodies Mediate Killing of Prostate Stem Cell Antigen-Expressing Tumor Cells by CD8+ and CD4+ T Cells," J Immunol., 2012, 189:3249-3259.

Grada et al., "TanCAR: A Novel Bispecific Chimeric Antigen Receptor for Cancer Immunotherapy," Molecular Therapy-Nucleic Acids, Jan. 1, 2013, 2:e105.

Hong et al., "Successful treatment of melanoma brain metastases with adoptive cell therapy," Clin Cancer Res, 2010, 16(19):4892-4898.

Hillerdal et al., "Systemic Treatment with CAR-engineered T cells against PSCA delays subcutaneous tumor growth and prolongs survival of mice," BMC Cancer, Jan. 2014, 14:30.

Hudecek et al., "The nonsignaling extracellular spacer domain of chimeric antigen receptors is decisive for in vivo antitumor activity," Cancer Immunology Research, Feb. 2015, 3(2):125-135.

Jonnalagadda et al., "Chimeric Antigen Receptors with Mutated IgG4 Fc Spacer Avoid Fc Receptor Binding and Improve T Cell Persistence and Antitumor Efficacy," Mol Ther,. Apr. 2015, 23(4):757-68.

Jonnalagadda et al., "Chimeric antigen receptors (CARs) incorporating mutations in the IgG4 Fc spacer region to eliminate Fc receptor recognition results in improved CAR T cell persistence and anti-tumor efficacy," Journal for Immuno Therapy of Cancer, 2013, 1(Suppl 1):P18.

Katari et al., "Engineered T cells for pancreatic cancer treatment," HPB., Sep. 2011, 13(9):643-650.

Klingemann, "Are natural killer cells superior CAR drivers?" Oncoimmunology, Jan. 1, 2014, 3(1):e28147.

Kunkele et al., "Functional Tuning of CARs Reveals Signaling Threshold above which CD8+ Antitumor Potency Is Attenuated due to Cell Fas-FasL-Dependent AICD," Cancer Immunology Research, Apr. 1, 2015, 3(4):368-379.

Lepin et al., "An affinity matured minibody for PET imaging of prostate stem cell antigen (PSCA)-expressing tumors," Eur J Nucl Med Mol Imaging., 2010, 37:1529-1538.

Long et al., "4-1BB costimulation ameliorates T cell exhaustion induced by tonic signaling of chimeric antigen receptors," Nature Medicine, May 4, 2015, 21(6):581-590.

Ohno et al., "Antigen-binding specificities of antibodies are primarily determined by seven residues of VH," Proc Natl Acad Sci USA., May 1985, 82:2945-2949.

Priceman et al., "Co-stimulatory signaling determines tumor antigen sensitivity and persistence of CAR T cells targeting PSCA+ metastatic prostate cancer," Oncoimmunology, 2018, 7(2):e1380764.

Porter et al., "Chimeric Antigen Receptor-Modified T Cells in Chronic Lymphoid Leukemia" New England Journal of Medicine, Aug. 25, 2011, 365(8):725-733.

Pule et al., "A Chimeric T cell antigen receptor that augments cytokine release and supports clonal expansion of primary human T cells," Molecular Therapy: The Journal of the American Society of Gene Therapy, Nov. 2005, 12(5):933-941.

(56) References Cited

OTHER PUBLICATIONS

Rudikoff et al., "Single amino acid substitution altering antigen-binding specificity," Proc Nat Acad Sci USA Immunology., 1982, 79:1979-1983.

Sampson et al., "EGFRvIII mCAR-modified T-cell therapy cures mice with established intracerebral glioma and generates host immunity against tumor-antigen loss," Clin Cancer Res., Feb. 15, 2014, 20(4):972-94.

Shi et al., "Chimeric antigen receptor for adoptive immunotherapy of cancer: latest research and future prospects," Molecular Cancer, Sep. 2014, 13:219.

Tang et al., "The Foxp3+ regulatory T cell: a jack of all trades, master of regulation," Nat Immunol., 2008, 9(3):239-244.

Vajdos et al., "Comprehensive functional maps of the antigen-binding site of an anti-ErbB2 antibody obtained with shotgun scanning mutagenesis," J Mol Biol., Jul. 5, 2002, 320(2):415-428.

Yaghoubi, "Noninvasive detection of therapeutic cytolytic T cells with 18F-FHBG PET in a patient with glioma," Nat Clin Pract Oncol, Jan. 2009, 6(1):53-58.

Zhong et al., "Chimeric Antigen Receptors Combining 4-1BB and CD28 Signaling Domains Augment P13kinase/AKT/Bcl-XL Activation and CD8+ T cell-mediated Tumor Eradication," Mol Ther., 2010, 18(2):413-420.

International Preliminary Report on Patentability in International Application No. PCT/US2016/055761, dated Apr. 10, 2018, 12 pages.

International Search Report and Written Opinion in International Application No. PCT/US2016/055761, dated Feb. 14, 2017, 20 pages.

Frigault et al. "Identification of chimeric antigen receptors that mediate constitutive or inducible proliferation of T cells," Cancer Immunol Res., 2015, 3(4):356-367.

Craft et al., "Evidence for clonal outgrowth of androgen-independent prostate cancer cells from androgen-dependent tumors through a two-step process," Cancer Res., 1999, 59(19):5030-5036.

Wang et al., "Engraftment of human central memory-derived effector CD8+ T cells in immunodeficient mice," Blood, 2011, 117(6):1888-1898.

Cooper et al., "T-cell clones can be rendered specific for CD19: toward the selective augmentation of the graft-versus-B-lineage leukemia effect," Blood 2003, 101:1637-1644.

* cited by examiner

FIG. 4A
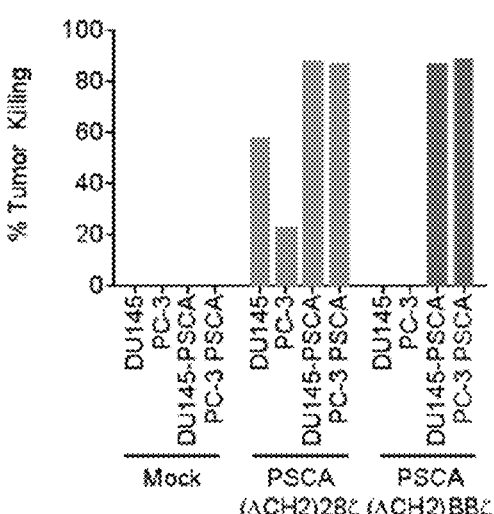
FIG. 4B
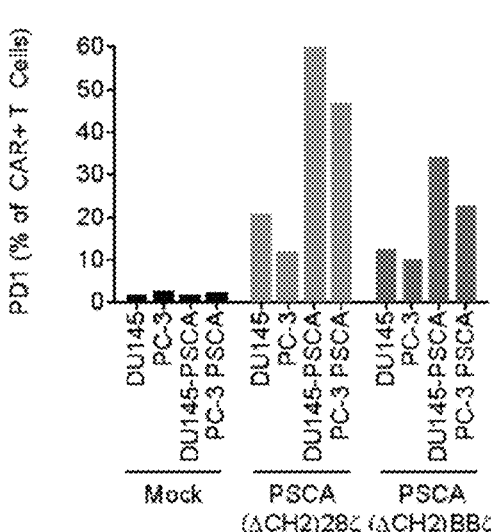
FIG. 4C
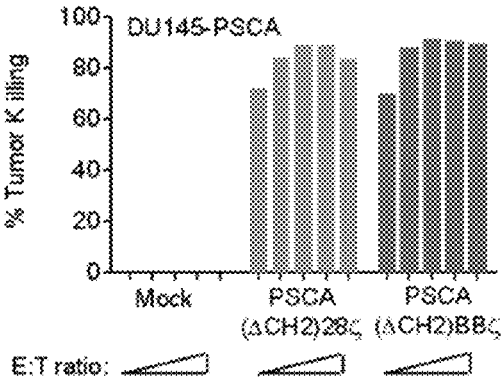
FIG. 4D
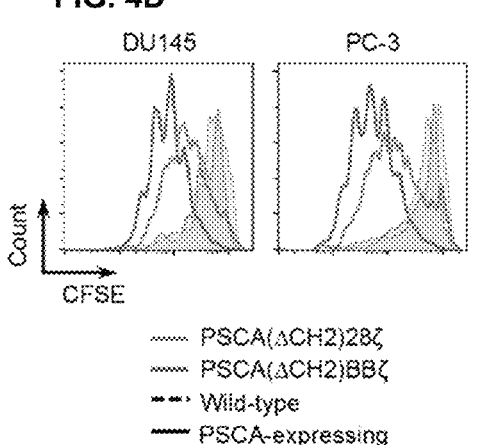
FIG. 4E
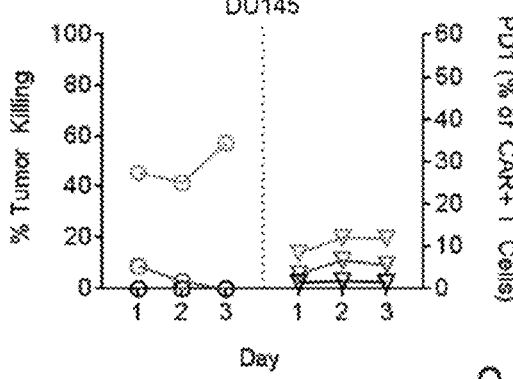
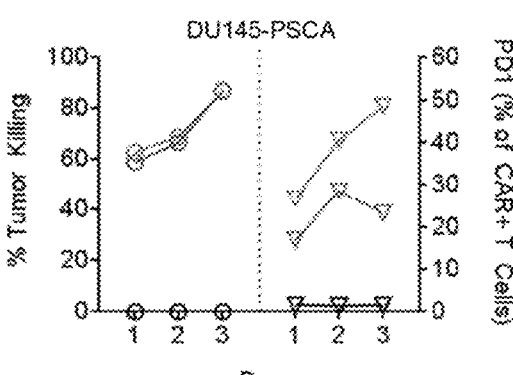

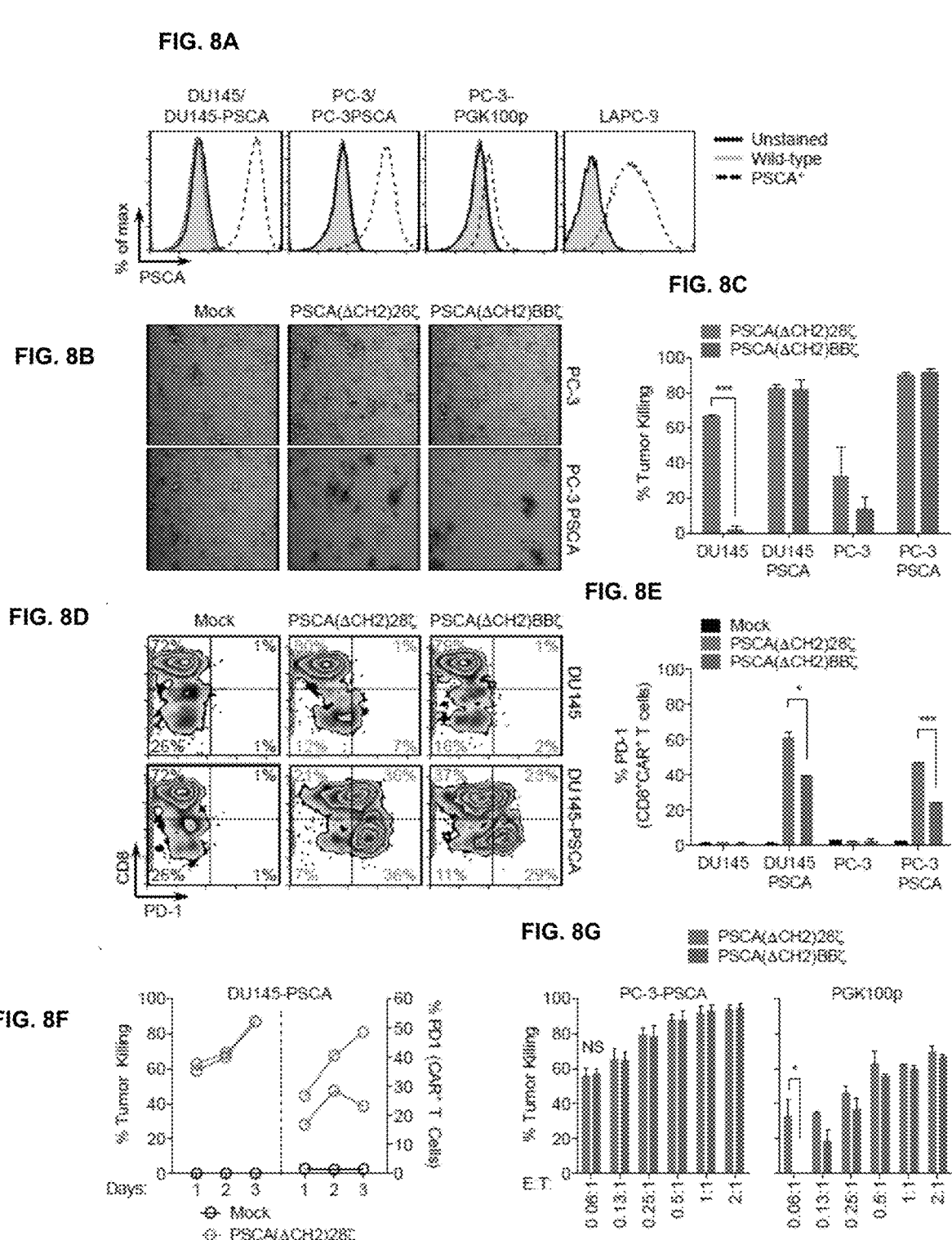

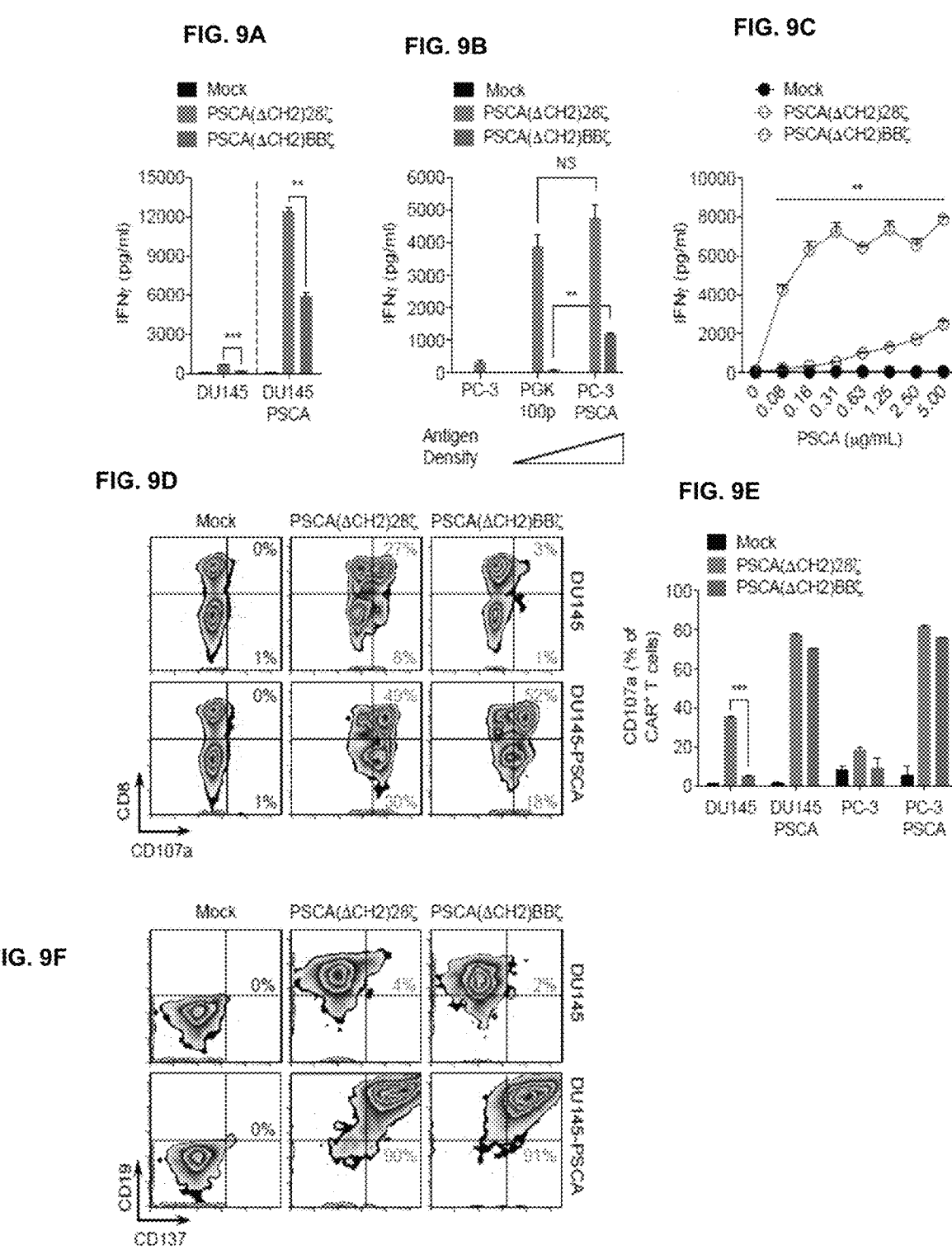

FIG. 11C          FIG. 11D

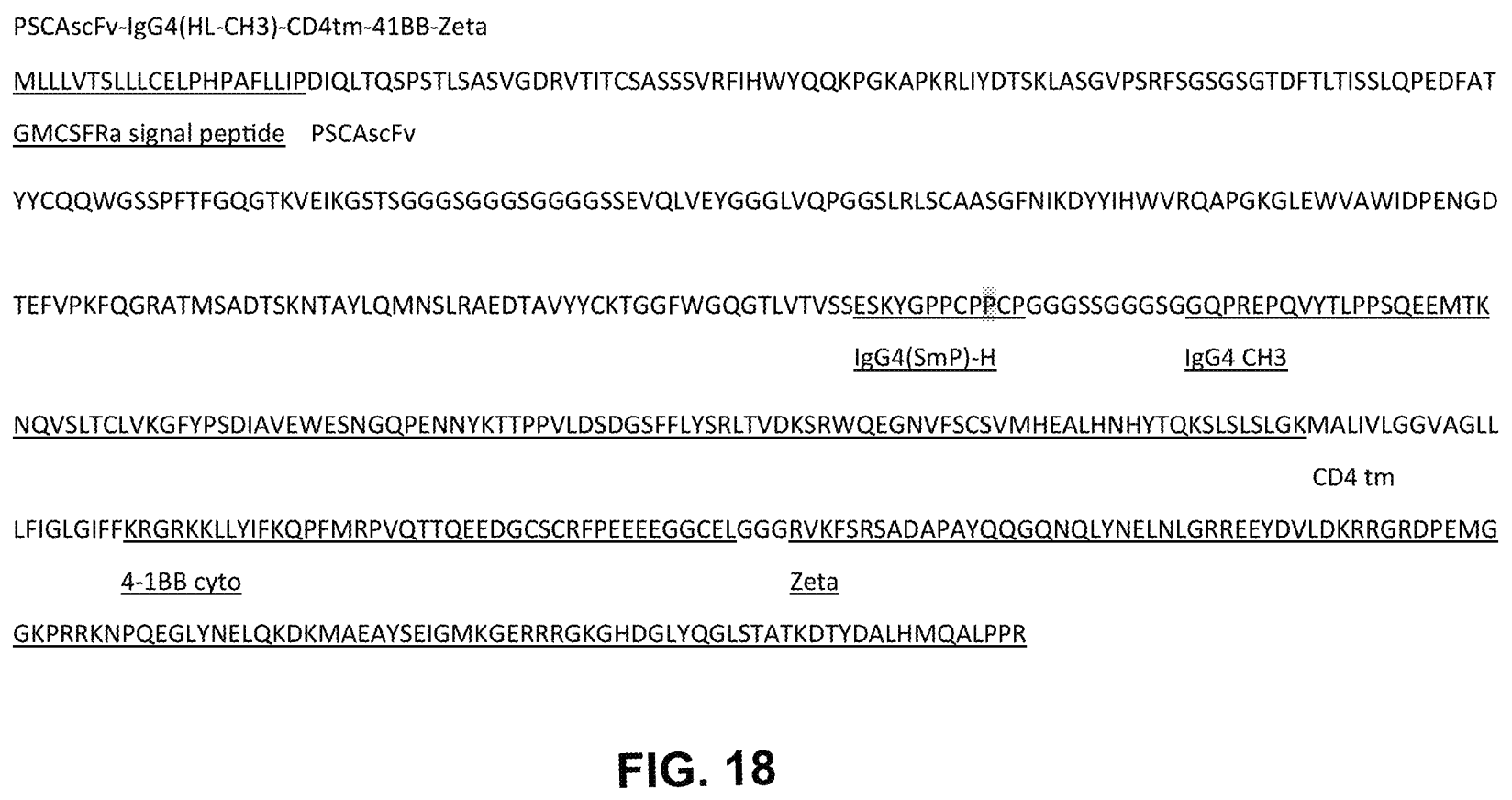

PSCAscFv-IgG4(HL-CH3)-CD4tm-41BB-Zeta

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT

GMCSFRa signal peptide   PSCAscFv

YYCQQWGSSPFTFGQGTKVEIKGSTSGGGSGGGSGGGGSSEVQLVEYGGGLVQPGGSLRLSCAASGFNIKDYYIHWVRQAPGKGLEWVAWIDPENGD

TEFVPKFQGRATMSADTSKNTAYLQMNSLRAEDTAVYYCKTGGFWGQGTLVTVSSESKYGPPCPPCPGGGSSGGGSGGQPREPQVYTLPPSQEEMTIK

IgG4(SmP)-H          IgG4 CH3

NQVSLTCLVKGFYPSDIAVEWESNGQPENNYKTTPPVLDSDGSFFLYSRLTVDKSRWQEGNVFSCSVMHEALHNHYTQKSLSLSLGKMALIVLGGVAGLL

CD4 tm

LFIGLGIFFKRGRKKLLYIFKQPFMRPVQTTQEEDGCSCRFPEEEEGGCELGGGRVKFSRSADAPAYQQGQNQLYNELNLGRREEYDVLDKRRGRDPEMG 4-1BB cyto                                          Zeta

GKPRRKNPQEGLYNELQKDKMAEAYSEIGMKGERRRGKGHDGLYQGLSTATKDTYDALHMQALPPR

FIG. 18

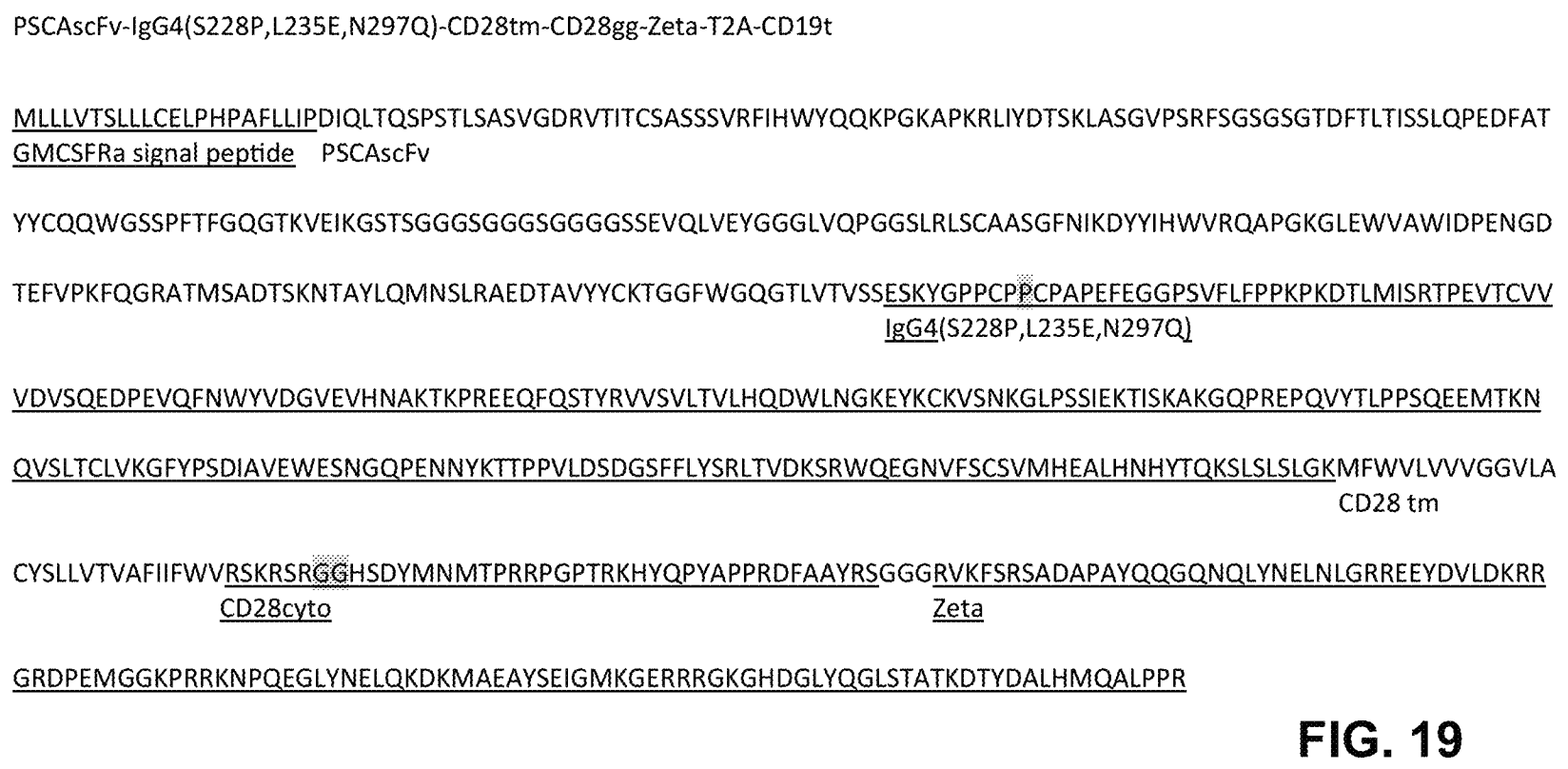

PSCAscFv-IgG4(S228P,L235E,N297Q)-CD28tm-CD28gg-Zeta-T2A-CD19t

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT
GMCSFRa signal peptide  PSCAscFv YYCQQWGSSPFTFGQGTKVEIKGSTSGGGSGGGSGGGSSEVQLVEYGGGLVQPGGSLRLSCAASGFNIKDYYIHWVRQAPGKGLEWVAWIDPENGD TEFVPKFQGRATMSADTSKNTAYLQMNSLRAEDTAVYYCKTGGFWGQGTLVTVSSESKYGPPCPPCPAPEFEGGPSVFLFPPKPKDTLMISRTPEVTCVV
                                                                                                IgG4(S228P,L235E,N297Q)

VDVSQEDPEVQFNWYVDGVEVHNAKTKPREEQFQSTYRVVSVLTVLHQDWLNGKEYKCKVSNKGLPSSIEKTISKAKGQPREPQVYTLPPSQEEMTKN

QVSLTCLVKGFYPSDIAVEWESNGQPENNYKTTPPVLDSDGSFFLYSRLTVDKSRWQEGNVFSCSVMHEALHNHYTQKSLSLSLGKMFWVLVVVGGVLA
                                                                                                CD28 tm

CYSLLLVTVAFIIFWVRSKRSRGGHSDYMNMTPRRPGPTRKHYQPYAPPRDFAAYRSGGGRVKFSRSADAPAYQQGQNQLYNELNLGRREEYDVLDKRR
CD28cyto                                                                                         Zeta

GRDPEMGGKPRRKNPQEGLYNELQKDKMAEAYSEIGMKGERRRGKGHDGLYQGLSTATKDTYDALHMQALPPR

FIG. 19

PSCAscFv-Linker-CD4tm-41BB-Zeta

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT

GMCSFRa signal peptide    PSCAscFv

YYCQQWGSSPFTFGQGTKVEIKGSTSGGGSGGGGSGGGGSSEVQLVEYGGGLVQPGGSLRLSCAASGFNIKDYYIHWVRQAPGKGLEWVAWIDPENGD

TEFVPKFQGRATMSADTSKNTAYLQMNSLRAEDTAVYYCKTGGFWGQGTLVTVSSGGGGSGGGGSGMALIVLGGVAGLLLFIGLGIFFKRGRKKLLYIF

Linker          CD4 tm           4-1BB cyto

KQPFMRPVQTTQEEDGCSCRFPEEEEGGCELGGGRVKFSRSADAPAYQQGQNQLYNELNLGRREEYDVLDKRRGRDPEMGGKPRRKNP

Zeta

QEGLYNELQKDKMAEAYSEIGMKGERRRGKGHDGLYQGLSTATKDTYDALHMQALPPR

FIG. 20

PSCAscFv-IgG4(HL-CH3)-CD28tm-CD28gg-Zeta

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT

GMCSFRa signal peptide    PSCAscFv

YYCQQWGSSPFTFGQGTKVEIKGSTSGGGSGGGSGGGSSEVQLVEYGGGLVQPGGSLRLSCAASGFNIKDYYIHWVRQAPGKGLEWVAWIDPENGD

TEFVPKFQGRATMSADTSKNTAYLQMNSLRAEDTAVYYCKTGGFWGQGTLVTVSSESKYGPPCPCPGGGSSGGGSGGGQPREPQVYTLPPSQEEMTK

IgG4(SmP)-H    Linker      IgG4-CH3

NQVSLTCLVKGFYPSDIAVEWESNGQPENNYKTTPPVLDSDGSFFLYSRLTVDKSRWQEGNVFSCSVMHEALHNHYTQKSLSLSLGKMFWVLVVVGGVL

CD28 tm

ACYSLLVTVAFIIFWVRSKRSRGGHSDYMNMTPRRPGPTRKHYQPYAPPRDFAAYRSGGGRVKFSRSADAPAYQQGQNQLYNELNLGRREEYDVLDKR

CD28cyto                                                    Zeta

RGRDPEMGGKPRRKNPQEGLYNELQKDKMAEAYSEIGMKGERRRGKGHDGLYQGLSTATKDTYDALHMQALPPR

FIG. 21

PSCAscFv-IgG4(S228P,L235E,N297Q)-CD4tm-41BB-Zeta

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT

GMCSFRa signal peptide    PSCAscFv

YYCQQWGSSPFTFGQGTKVEIKGSTSGGGSGGGSGGGSSEVQLVEYGGGLVQPGGSLRLSCAASGFNIKDYYIHWVRQAPGKGLEWVAWIDPENGD

TEFVPKFQGRATMSADTSKNTAYLQMNSLRAEDTAVYYCKTGGFWGQGTLVTVSSESKYGPPCP□CPAPEFEGGPSVFLFPPKPKDTLMISRTPEVTCVV

IgG4(S228P,L235E,N297Q)

VDVSQEDPEVQFNWYVDGVEVHNAKTKPREEQFQSTYRVVSVLTVLHQDWLNGKEYKCKVSNKGLPSSIEKTISKAKGQPREPQVYTLPPSQEEMTKN

QVSLTCLVKGFYPSDIAVEWESNGQPENNYKTTPPVLDSDGSFFLYSRLTVDKSRWQEGNVFSCSVMHEALHNHYTQKSLSLSLGKMALIVLGGVAGLLL

CD4 tm

FIGLGIFFKRGRKKLLYIFKQPFMRPVQTTQEEDGCSCRFPEEEEGGCELGGGRVKFSRSADAPAYQQGQNQLYNELNLGRREEYDVLDKRRGRDPEMGG

Zeta

KPRRKNPQEGLYNELQKDKMAEAYSEIGMKGERRRGKGHDGLYQGLSTATKDTYDALHMQALPPR 4-1BB cyto

FIG. 22

PSCAscFv-Linker-CD28tm-CD28gg-Zeta

MLLLVTSLLLCELPHPAFLLIPDIQLTQSPSTLSASVGDRVTITCSASSSVRFIHWYQQKPGKAPKRLIYDTSKLASGVPSRFSGSGSGTDFTLTISSLQPEDFAT

GMCSFRa signal peptide     PSCAscFv

YYCQQWGSSPFTFGQGTKVEIKGSTSGGGSGGGGSGGGGSSEVQLVEYGGGLVQPGGSLRLSCAASGFNIKDYYIHWVRQAPGKGLEWVAWIDPENGD

TEFVPKFQGRATMSADTSKNTAYLQMNSLRAEDTAVYYCKTGGFWGQGTLVTVSSGGGGSGGGGSGMFWVLVVVGGVLACYSLLVTVAFIIFWVRSKRS

Linker       CD28 tm      CD28cyto

RGGHSDYMNMTPRRPGPTRKHYQPYAPPRDFAAYRSGGGRVKFSRSADAPAYQQGQNQLYNELNLGRREEYDVLDKRRGRDPEMGGKPRRKNPQE

Zeta

GLYNELQKDKMAEAYSEIGMKGERRRGKGHDGLYQGLSTATKDTYDALHMQALPPR

FIG. 23

CHIMERIC ANTIGEN RECEPTORS TARGETED TO PSCA

CROSS-REFERENCE TO RELATED APPLICATION

This application is a continuation of U.S. application Ser. No. 15/766,674, filed Apr. 6, 2018, now U.S. Pat. No. 11,466,097, which is a National Stage Application under 35 U.S.C. § 371 and claims the benefit of International Application No. PCT/US2016/055761, filed Oct. 6, 2016, which claims the benefit of U.S. Provisional Application No. 62/238,062, filed Oct. 6, 2015. The disclosure of the foregoing applications are hereby incorporated by reference in their entirety.

SEQUENCE LISTING

This application contains a Sequence Listing that has been submitted electronically as an XML file named "40056-0025002_SL_ST26.XML." The XML file, created on Jul. 24, 2023, is 50,144 bytes in size. The material in the XML file is hereby incorporated by reference in its entirety.

BACKGROUND

Prostate Cancer (PCa) is the third most common cancer type in the United States, with over 200,000 new cases projected to be diagnosed this year. In approximately 80% of PCa patients, tumor phenotype includes overexpression of prostate stem cell antigen (PSCA). Furthermore, PSCA is expressed on nearly 100% of bone metastatic prostate cancers, making it a theoretically attractive immunotherapeutic target. Recent clinical trials with CARs targeting CD19 for B-cell malignancies have demonstrated impressive results, yet replicating this success with other antigen targets remains elusive. Immunotherapy against solid tumors poses a more difficult tumor challenge due to the lack of such restricted antigen expression (i.e., CD19 for B cell malignancies) and the presence of an immunosuppressive microenvironment that can significantly hinder CAR efficacy. Importantly, there have been instances of on-target, off-tumor toxicity due to low levels of antigen expression on normal tissue.

While the basic components needed to create a CAR capable of binding to a desired target are reasonably well understood, it is challenging to design a CAR that has the qualities required for use in a safe and effective therapy. For example, it is important to avoid excessive activity against non-cancerous cells that express a low level of the target or do not express the target at all. Is also important to avoid eliciting a high level of cytokine production which can elicit undesirable off-tumor effects. Other factors that can impact therapeutic potential include, but are not limited to, the replicative capacity and life-span of the T cells expressing the CAR and the overall effector function of the T cells expressing the CAR required for a robust anti-tumor response.

SUMMARY

Described herein are chimeric transmembrane immunoreceptors (chimeric antigen receptors or "CARs") which comprise an extracellular domain, a transmembrane region and an intracellular signaling domain. The extracellular domain includes an scFv targeted against PSCA. The CAR described herein are useful for treating prostate cancer and prostate cancer bone metastasis.

In addition to an scFv target to PSCA, the extracelluar domain includes a spacer comprising, for example, a portion of the human IgG4 Fc domain. The transmembrane portion of the CAR includes, for example, a CD4 transmembrane domain, a CD8 transmembrane domain, a CD28 transmembrane domain, a CD3 transmembrane domain or a 4IBB transmembrane domain. The intracellular signaling domain includes the signaling domain from the zeta chain of the human CD3 complex (CD3$\zeta$) and a costimulatory domain (e.g., the OX40, CD28, CD28gg or 4-1BB (CD137) costimulatory domain. The extracellular domain enables the CAR, when expressed on the surface of a T cell, to direct T cell activity to those cells expressing a PSCA. Such cells include prostate cancer cells. The inclusion of a costimulatory domain in series with (but not necessarily immediately adjacent to) CD3$\zeta$ in the intracellular region enables the T cell to receive co-stimulatory signals. T cells, for example, patient-specific, autologous T cells can be engineered to express the CARs described herein and the engineered cells can be expanded and used in ACT. Various T cell subsets can be used. In addition, the CAR can be expressed in other immune cells such as NK cells. Where a patient is treated with an immune cell expressing a CAR described herein the cell can be an autologous or allogenic T cell. In some cases, the cells used are CD4+ and CD8+ central memory T cells ($T_{CM}$), which are CD45RA-CD62L+, or $T_{CM/SCM/N}$ cells (CD45RA+CD62L+) and the use of such cells can improve long-term persistence of the cells after adoptive transfer compared to the use of other types of patient-specific T cells. Importantly, the overall design of the CAR avoids unwanted activity against non-cancerous cells, including non-cancerous cells expressing only a relatively low level of PSCA.

The PSCA scFv can include the sequence: DIQLTQSP-STLSASVGDRVTITCSASSSV RFIHWYQQKPGKAPKRLIYDTSKLASG VPSRFSGSGSGTDFTLTISSLQPEDFA-TYYCQQWGSSPFTFGQGTKVEIKGSTSGG GSGGGSGGGGSSEVQLVEYGGGLVQPGGSLRLS-CAASGFNIKDYYIHWVRQAPG KGLEWVAWIDPENGDTEFVPKFQGRATMSADTSKN-TAYLQMNSLRAEDTAVY YCKTGGFWGQGTLVTVSS (SEQ ID NO: 38) or a variant thereof having up to 5 amino acid substitutions (e.g., conservative substitutions).

Described herein is a nucleic acid molecule encoding a CAR comprising: an scFv directed against PSCA (e.g., SEQ ID NO:1) or a variant thereof having 1-5 (e.g., 1 or 2) amino acid modifications; a transmembrane domain selected from: a CD4 transmembrane domain or variant thereof having 1-10 (e.g., 1 or 2) amino acid modifications, a CD8 transmembrane domain or variant thereof having 1-5 (e.g., 1 or 2) amino acid modifications, a CD28 transmembrane domain or a variant thereof having 1-5 (e.g., 1 or 2) amino acid modifications, and a CD3$\zeta$ transmembrane domain or a variant thereof having 1-10 (e.g., 1 or 2) amino acid modifications; a costimulatory domain; and CD3$\zeta$ signaling domain of a variant thereof having 1-5 (e.g., 1 or 2) amino acid modifications. A spacer region is located between the scFv and the transmembrane domain. The spacer region, described in greater detail below, can include all or part of a human Fc region.

In some embodiments: nucleic acid molecule expresses a polypeptide comprising an amino acid sequence selected from SEQ ID NOs: 26-37; the chimeric antigen receptor comprises an amino acid sequence selected from SEQ ID NOs: 26-37 with 1-5 (e.g., 1 or 2) amino acid modifications (e.g., substitutions).

Also disclosed is a population of human T cells transduced by a vector comprising an expression cassette encoding a chimeric antigen receptor, wherein chimeric antigen receptor comprises an scFv directed to PSCA which includes a 4-1BB co-stimulatory domain. In various embodiments: the population of human T cells comprise a vector expressing a chimeric antigen receptor comprising an amino acid sequence selected from SEQ ID NOs: 26-37; the population of human T cells comprises of central memory T cells ($T_{CM}$) (e.g., at least 20%, 30%, 40%, 50% 60%, 70%, 80% of the cells are $T_{CM}$ cells; at least 15%, 20%, 25%, 30%, 35% of the Tc cells are CD4+ and at least 15%, 20%, 25%, 30%, 35% of the $T_{CM}$ cells are CD8+ cells).

Also described is a method of treating cancer in a patient comprising administering a population of autologous or allogeneic human T cells (e.g., autologous or allogenic T cells comprising T cells, e.g., at least 20%, 30%, 40%, 50% 60%, 70%, 80% of the cells are $T_{CM}$ cells; at least 15%, 20%, 25%, 30%, 35% of the $T_{CM}$ cells are CD4+ and at least 15%, 20%, 25%, 30%, 35% of the $T_{CM}$ cells are CD8+ cells) transduced by a vector comprising an expression cassette encoding a chimeric antigen receptor, wherein chimeric antigen receptor comprises an amino acid sequence selected from SEQ ID NOs: 26-37. In various embodiments: the population of human T cells comprise central memory T cells; the cancer is glioblastoma; and the transduced human T cells where prepared by a method comprising obtaining T cells from the patient, treating the T cells to isolate central memory T cells, and transducing at least a portion of the central memory cells to with a viral vector comprising an expression cassette encoding a chimeric antigen receptor, wherein chimeric antigen receptor comprises an amino acid sequence selected from SEQ ID NOs: 26-37.

Also described is: a nucleic acid molecule encoding an polypeptide comprising an amino acid sequence that is at least 95% identical to an amino acid sequence selected from SEQ ID NOs 26-37; a nucleic acid molecule encoding an polypeptide comprising an amino acid sequence that is identical to an amino acid sequence selected from SEQ ID NOs: 26-37 except for the presence of no more than 5 amino acid substitutions, deletions or insertions; a nucleic acid molecule encoding an polypeptide comprising an amino acid sequence that is identical to an amino acid sequence selected from SEQ ID NOs: 26-37 except for the presence of no more than 5 amino acid substitutions; and a nucleic acid molecule encoding an polypeptide comprising an amino acid sequence that is identical to an amino acid sequence selected from SEQ ID NOs: 26-37 except for the presence of no more than 2 amino acid substitutions.

T cells expressing a CAR targeted to PSCA can be useful in treatment of prostate cancer, including hormone refractory prostate cancer and metastases of prostate cancer, including bone liver, and lung metastases, as well as other cancers that express a PSCA, which include, but are not limited to pancreatic, bladder, colon, and glioblastoma (primary brain). Thus, this disclosure includes methods for treating cancer using T cells expressing a CAR described herein.

This disclosure also nucleic acid molecules that encode any of the CARs described herein (e.g., vectors that include a nucleic acid sequence encoding one of the CARs) and isolated T lymphocytes that express any of the CARs described herein.

The CAR described herein can include a spacer region located between the PSCA targeting domain (i.e., scFv recognizing PSCA or variant thereof) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |
| IgG4 hinge (S→P) (S228P) | 12 aa | ESKYGPPCₓCP (SEQ ID NO: 3) |
| IgG4 hinge | 12 aa | ESKYGPPCPSCP (SEQ ID NO: 4) |
| IgG4 hinge + linker | 22 aa | ESKYGPPCPPCPGGGSSGGGSG (SEQ ID NO: 5) |
| CD28 hinge | 39 aa | IEVMYPPPYLDNEKSNGTIIHVKGKHL CPSPLFPGPSKP (SEQ ID NO: 6) |
| CD8 hinge-48 aa | 48 aa | AKPTTTPAPRPPTPAPTIASQPLSLR PEACRPAAGGAVHTRGLDFACD (SEQ ID NO: 7) |
| CD8 hinge-45 aa | 45 aa | TTTPAPRPPTPAPTIASQPLSLRPEA CRPAAGGAVHTRGLDFACD (SEQ ID NO: 8) |
| IgG4 (HL-CH3) | 129 aa | ESKYGPPCPPCPGGGSSGGGSGGQPR EPQVYTLPPSQEEMTKNQVSLTCLVK GFYPSDIAVEWESNGQPENNYKTTPP VLDSDGSFFLYSRLTVDKSRWQEGNV FSCSVMHEALHNHYTQKSLSLSLGK SEQ ID NO: 9) |
| IgG4 (S228P, L235E, N297Q) | 229 aa | ESKYGPPCPPCPAPEₓGGPSVFLFP PKPKDTLMISRTPEVTCVVVDVSQED PEVQFNWYVDGVEVHNAKTKPREEQF QSTYRVVSVLTVLHQDWLNGKEYKCK VSNKGLPSSIEKTISKAKGQPREPQV YTLPPSQEEMTKNQVSLTCLVKGFYP SDIAVEWESNGQPENNYKTTPPVLDS DGSFFLYSRLTVDKSRWQEGNVFSCS VMHEALHNHYTQKSLSLSLGK (SEQ ID NO: 10) |
| IgG4 (CH3) | 107 aa | GQPREPQVYTLPPSQEEMTKNQVSLT CLVKGFYPSDIAVEWESNGQPENNYK TTPPVLDSDGSFFLYSRLTVDKSRWQ EGNVFSCSVMHEALHNHYTQKSLSLS LGK (SEQ ID NO: 12) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one ore more amino acid modifications, for example, 1, 2, 3, 4 or 5 substitutions, e.g., substitutions that reduce off-target binding.

An "amino acid modification" refers to an amino acid substitution, insertion, and/or deletion in a protein or peptide sequence. An "amino acid substitution" or "substitution"

refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In certain embodiments, the spacer is derived from an IgG1, IgG2, IgG3, or IgG4 that includes one or more amino acid residues substituted with an amino acid residue different from that present in an unmodified spacer. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof. In this numbering scheme, described in greater detail below, the first amino acid in the IgG4 (L235E,N297Q) spacer in Table 1 is 219 and the first amino acid in the IgG4 (HL-CH3) spacer in Table 1 is 219 as is the first amino acid in the IgG hinge sequence and the IgG4 hinge linker (HL) sequence in Table 1

In some embodiments, the modified spacer is derived from an IgG1, IgG2, IgG3, or IgG4 that includes, but is not limited to, one or more of the following amino acid residue substitutions: C220S, C226S, S228P, C229S, P230S, E233P, V234A, L234V, L234F, L234A, L235A, L235E, G236A, G237A, P238S, S239D, F243L, P247I, S267E, H268Q, S280H, K290S, K290E, K290N, R292P, N297A, N297Q, S298A, S298G, S298D, S298V, T299A, Y300L, V305I, V309L, E318A, K326A, K326W, K326E, L328F, A330L, A330S, A331S, P331S, I332E, E333A, E333S, E333S, K334A, A339D, A339Q, P396L, or a combination thereof.

In certain embodiments, the modified spacer is derived from IgG4 region that includes one or more amino acid residues substituted with an amino acid residue different from that present in an unmodified region. The one or more substituted amino acid residues are selected from, but not limited to, one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified spacer is derived from an IgG4 region that includes, but is not limited to, one or more of the following amino acid residue substitutions: 220S, 226S, 228P, 229S, 230S, 233P, 234A, 234V, 234F, 234A, 235A, 235E, 236A, 237A, 238S, 239D, 243L, 247I, 267E, 268Q, 280H, 290S, 290E, 290N, 292P, 297A, 297Q, 298A, 298G, 298D, 298V, 299A, 300L, 305I, 309L, 318A, 326A, 326W, 326E, 328F, 330L, 330S, 331S, 331S, 332E, 333A, 333S, 333S, 334A, 339D, 339Q, 396L, or a combination thereof, wherein the amino acid in the unmodified spacer is substituted with the above identified amino acids at the indicated position.

For amino acid positions in immunoglobulin discussed herein, numbering is according to the EU index or EU numbering scheme (Kabat et al. 1991 Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al. 1969 *Proc Natl Acad Sci USA* 63:78-85).

A variety of transmembrane domains can be used in the. Table 2 includes examples of suitable transmembrane domains. Where a spacer domain is present, the transmembrane domain is located carboxy terminal to the spacer domain.

TABLE 2

Examples of Transmembrane Domains

| Name | Accession | Length | Sequence |
|---|---|---|---|
| CD3z | J04132.1 | 21 aa | LCYLLDGILFIYGVILT ALFL (SEQ ID NO: 13) |
| CD28 | NM_ 006139 | 27 aa | FWVLVVVGGVLACYSLL VTVAFIIFWV (SEQ ID NO: 14) |
| CD28(M) | NM_ 006139 | 28 aa | MFWVLVVVGGVLACYSL LVTVAFIIFWV (SEQ ID NO: 15) |
| CD4 | M35160 | 22 aa | MALIVLGGVAGLLLFI GLGIFF (SEQ ID NO: 16) |
| CD8tm | NM_ 001768 | 21 aa | IYIWAPLAGTCGVLL LSLVIT (SEQ ID NO: 17) |
| CD8tm2 | NM_ 001768 | 23 aa | IYIWAPLAGTCGVLLL SLVITLY (SEQ ID NO: 18) |
| CD8tm3 | NM_ 001768 | 24 aa | IYIWAPLAGTCGVLLL SLVITLYC (SEQ ID NO: 19) |
| 41BB | NM_ 001561 | 27 aa | IISFFLALTSTALLFL LFFLTLRFSVV (SEQ ID NO: 20) |

Many of the CAR described herein include one or more (e.g., two) costimulatory domains. The costimulatory domain(s) are located between the transmembrane domain and the CD3ζ signaling domain. Table 3 includes examples of suitable costimulatory domains together with the sequence of the CD3ζ signaling domain.

TABLE 3

| CD3ζ Domain and Examples of Costimulatory Domains | | | |
|---|---|---|---|
| Name | Accession | Length | Sequence |
| CD3ζ | J04132.1 | 113 aa | RVKFSRSADAPAYQQGQNQLYN RELNLGREEYDVLDKRRGRDPE MGGKPRRKNPQEGLYNELQKDK MAEAYSEIGMKGERRRGKGHDG LYQGLSTATKDTYDALHMQAL PPR (SEQ ID NO: 21) |
| CD28 | NM_ 006139 | 42 aa | RSKRSRLLHSDYMNMTPRRPGP TRKHYQPYAPPRDFAAYRS (SEQ ID NO: 22) |
| CD28 gg* | NM_ 006139 | 42 aa | RSKRSRGGHSDYMNMTPRRPGP TRKHYQPYAPPRDFAAYRS (SEQ ID NO: 23) |
| 41BB | NM_ 001561 | 42 aa | KRGRKKLLYIFKQPFMRPVQT TQEEDGCSCRFPEEEEGGCEL (SEQ ID NO: 24) |
| OX40 | | 42 aa | ALYLLRRDQRLPPDAHKPPGG GSFRTPIQEEQADAHSTLAKI (SEQ ID NO: 25) |

The PSCA-CAR used in the studies described herein are those summarized in Table 4 (immature, including GMCSFRa signal sequence) in which the spacer domain and costimulatory domain(s) for each CAR are indicated. All of these include the A11 PSCA scFv. The IgG4(HL-CH3) spacer is also referred to as the IgG4ΔCH2 spacer. The mature sequences (lacking GMCSFRa signal sequence) for SEQ ID NOs: 26, 27, 28, 29, 30, and 31 are SEQ ID NOs: 32, 33, 43, 35, 36, and 37.

TABLE 4

| | Examples of CAR Targeting PSCA | | | | |
|---|---|---|---|---|---|
| Name | SEQ ID NO with signal/ without signal | FIGURE | Spacer | TM | Costimu- latory Domain(s) |
| PSCAscFv- IgG4(HL-CH3- CD4tm- 4IBB-zeta | 26/32 | 18 | IgG4(HL- CH3) (IgG4ΔCH2) | CD4 | 4-IBB |
| PSCAscFv- IgG4(EQ)- CD28tm- CD28gg-zeta | 27/33 | 19 | IgG4(EQ) | CD28 | CD28gg |
| PSCAscFv-L- CD4tm- 4IBB-zeta | 28/34 | 20 | L | CD4 | 4-IBB |
| PSCAscFv- IgG4(HL- CH3)— CD28tm- CD28gg-zeta | 28/35 | 21 | IgG4(HL- CH3) (IgG4ΔCH2) | CD28 | CD28gg |
| PSCAscFv- IgG4(EQ)- CD4tm- 4IBB-zeta | 30/36 | 22 | IgG4(EQ) | CD4 | 4-IBB |
| PSCAscFv-L- CD28tm- 4IBB-zeta | 31/37 | 23 | L | CD28 | CD28gg |

and having either: (a CD28 transmembrane domain and a CD28 co-stimulatory domain; or a CD4 transmembrane domain and a 4-IBB co-stimulatory domain. The constructs used a MB1 scFv or an A11 scFv. All constructs used a CD3ζ cytolytic domain. The T2A skip sequence separates the CAR from a truncated CD19 (CD19t) protein that is used to assess expression of the construct.

Figure 1:
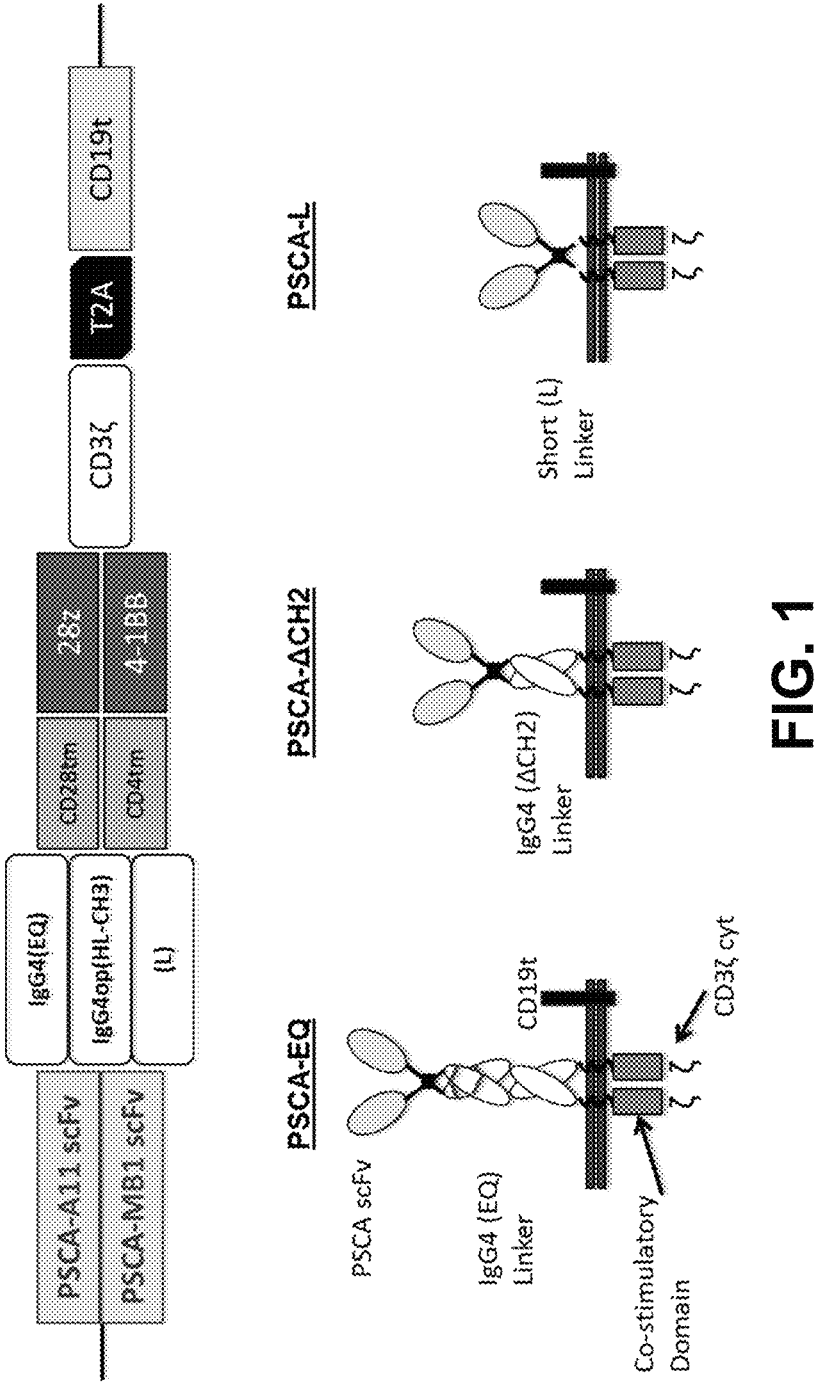
FIG. 1: Schematic diagram of CAR constructs with a variety of spacer regions (described in greater detail above)
Figure 2:
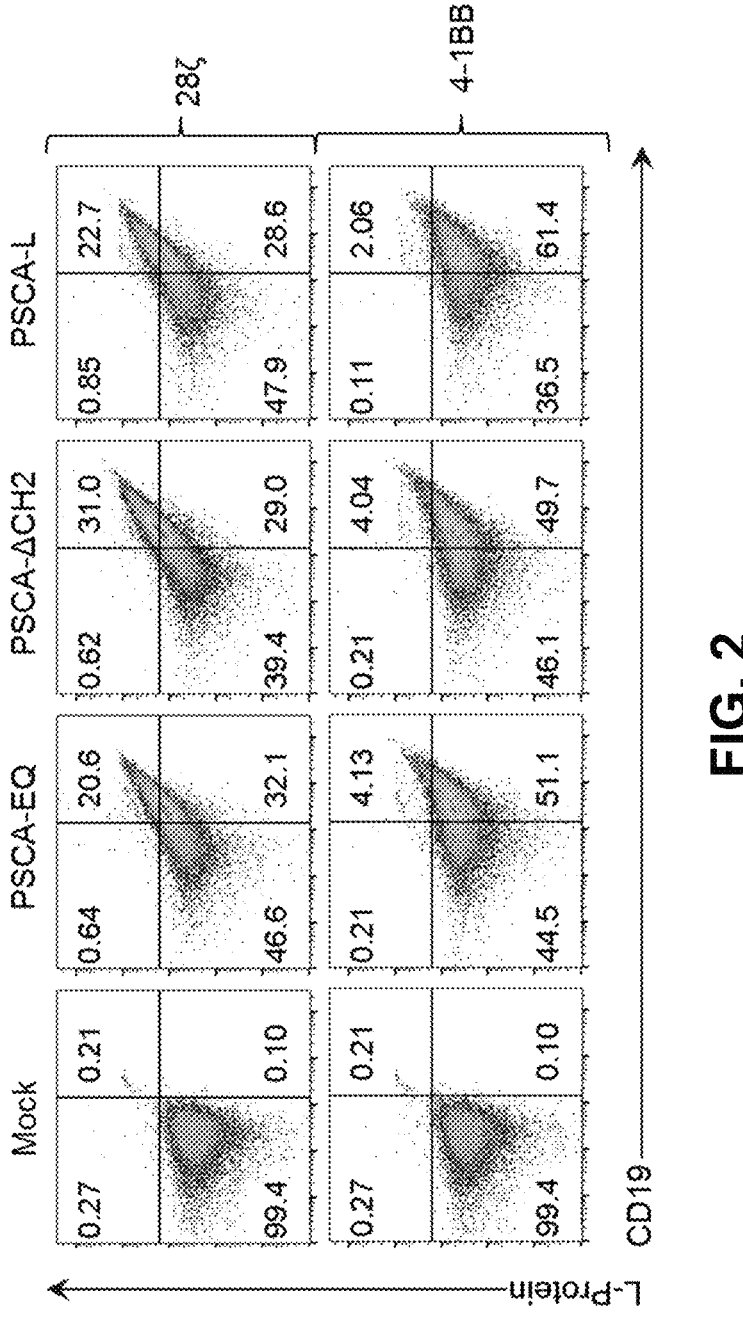

FIG. 2: Measurement of tCD19 and scFv (Protein L) expression data for the various constructs in FIG. 1.

FIG. 3A-3E: In vitro characterization of two different PSCA-CAR T cells against human prostate cancer cell lines. (FIG. 3A) Expression of PSCA in tumor cells engineered to express PSCA (LCL, PC-3, and DU145). (FIG. 3B-3C) CD107a degranulation and IFNγ production in CAR T cells following a 5 h co-culture with tumor target, measured by flow cytometry. (FIG. 3D-3E) IFNγ production by CAR T cells following a 24 h culture with recombinant PSCA protein or tumor targets, measured by ELISA.

FIG. 4A-4E: PSCA-CARs containing 4-1BB co-stimulatory domain demonstrate superior specificity, proliferation, and tumor cell killing capacity. Tumor killing (FIG. 4A) and PD-1 induction (FIG. 4B) in PSCA(ΔCH2)28z or PSCA (ΔCH2)BBz CAR T cells following a 72 h co-culture with tumor targets (DU145, PC-3, DU145-PSCA, and PC-3-PSCA) measured by flow cytometry. (FIG. 4C) Tumor killing with Effector:Tumor (E:T) ratio from 0.25:1-4:1. (FIG. 4D) CFSE proliferation of CAR T cells following a 72 h co-culture with tumor targets. (FIG. 4E) Kinetics of tumor killing and PD-1 induction in CAR T cells following a 1, 2 or 3 day co-culture with tumor targets (DU145, left; DU145-PSCA, right).

Figures 5A, 5B:
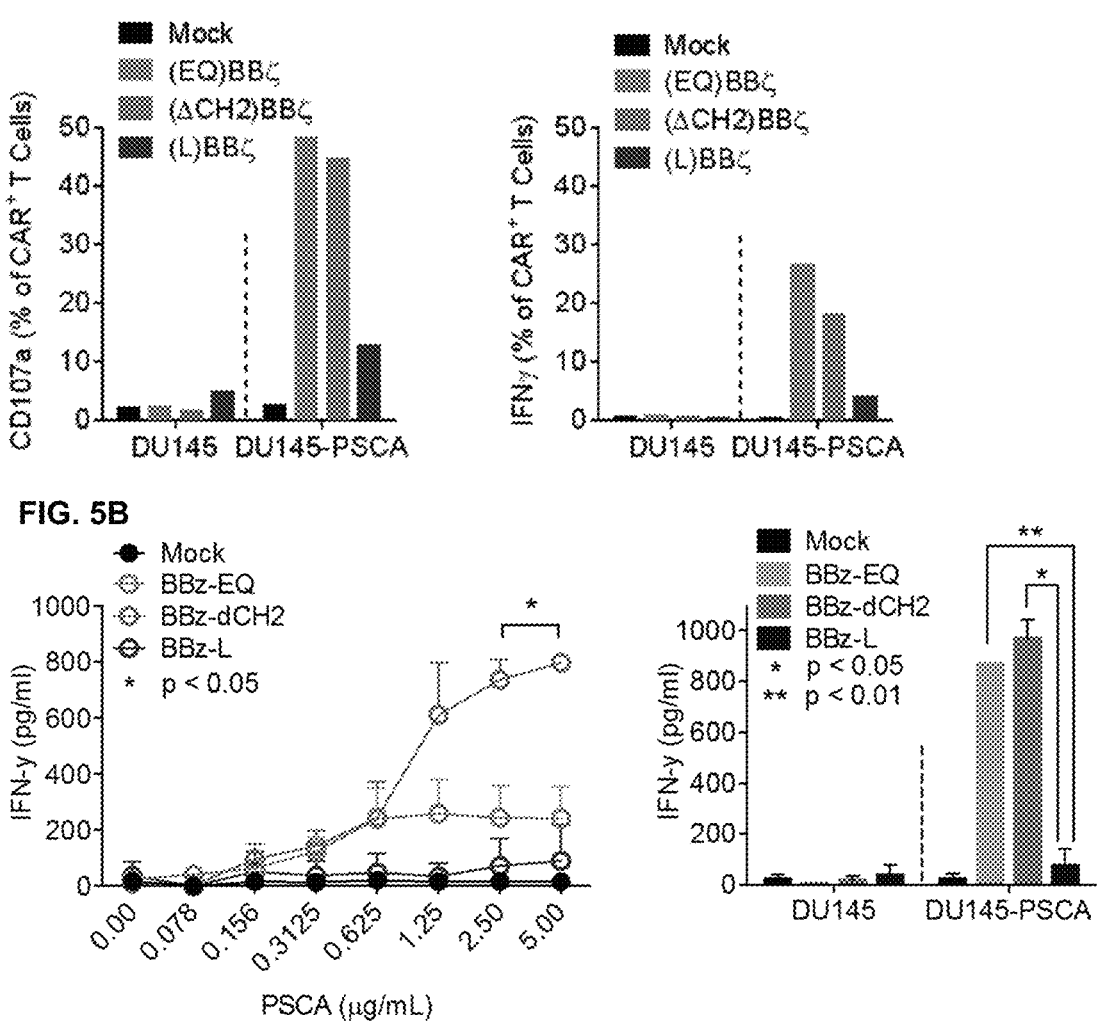

FIGS. 5A-5B: Extracellular spacer dictates in vitro PSCA-CAR functionality. (FIG. 5A) CD107a degranulation and IFNγ production in PSCA(EQ)BBz, PSCA(ΔCH2)BBz, and PSCA(L)BBz CAR T cells following a 5 h co-culture with tumor targets (DU145 and DU145-PSCA), measured by flow cytometry. (FIG. 5B) IFNγ in CAR T cells following a 24 h culture with recombinant PSCA protein or tumor targets, measured by ELISA.

FIG. 6A-6D: PSCA-CAR T cells demonstrate potent anti-tumor efficacy in prostate cancer xenograft and ortho-topic models. (FIG. 6A) PC-3-PSCA($2\times10^6$) cells were injected subcutaneously in NSG male mice, and when tumors reached ~30-50 mm3, CAR Tcm ($5\times10^6$) were injected intratumorally, and tumor growth was monitored by caliper measurements. (FIG. 6B) DU145-PSCA($2\times10^6$) cells were injected subcutaneously in NSG males, and CAR PBMC cells ($5\times10^6$) cells were intravenously delivered. (FIG. 6C) PC-3-PSCA($2\times105$) cells were injected intratibi-ally in NSG males, and CAR PBMC cells ($2\times10^6$ or $5\times106$) were intravenously delivered. (FIG. 6D) CAR T cell persis-tence in blood at 58 days post tumor injection in each group.

FIG. 7A-7D: PSCA-CAR T cells containing CD28 or 4-1BB co-stimulatory domains. (FIG. 7A) Diagram of the lentiviral expression cassette with PSCA-CARs containing the humanized scFv (A11 clone) targeting PSCA, with a 129 amino acid modified human IgG4 Fc linker (void of the CH2 domain, ΔCH2), a transmembrane domain (either CD28 or CD4), a cytoplasmic CD28 or 4-1BB costimulatory domain, and a cytolytic CD3z domain. A truncated non-signaling CD19 (CD19t) is separated from the CAR with a T2A ribosomal skip sequence for tracking CAR-expressing cells. (FIG. 7B) Mock (untransduced), PSCA(ΔCH2)28ζ, or PSCA(ΔCH2)BBζ CAR T cells were evaluated by flow cytometry for CD19t expression to detect lentiviral trans-duction of CARs (top) or Protein L to detect the scFv (bottom). (FIG. 7C) Ex vivo expansion kinetics for Mock and PSCA-CAR T cells over 25 days in culture. (FIG. 7D) Cell-surface expression of indicated cell-surface markers of PSCA-CAR T cells at end of ex vivo expansion as determined by flow cytometry. All data are representative of at least two independent experiments.

FIG. 8A-8G: PSCA-CARs containing a 4-1BB co-stimulatory domain show superior tumor targeting compared with CD28 co-stimulation in PSCA-CARs in vitro. (FIG. 8A) Histograms of PSCA expression in human prostate cancer cell lines, determined by flow cytometry. DU145 and PC-3 cell lines were lentivirally transduced to over-express human PSCA under the control of the EF1α promoter (see materials and methods). PC-3-PGK100p cell line was generated by expressing human PSCA under the control of the indicated mutant PGK promoter. LAPC-9 cells endogenously express human PSCA. (FIG. 8B) Snapshot images of a tumor killing assay comparing Mock, PSCA($\Delta$CH2)28$\zeta$, or PSCA($\Delta$CH2) BB$\zeta$ CAR T cells at a 1:1 effector:target ratio, assessed by light microscopy following a 3-day co-culture with PC-3 or PC-3-PSCA tumor cells. (FIG. 8C) Similar tumor killing assay as in (FIG. 8B), assessed by flow cytometry following a 3-day co-culture with indicated tumor targets. (FIG. 8D) Representative zebra plots of PD-1 expression in PSCA-CAR T cells following a 3-day co-culture with indicated tumor targets. (FIG. 8E) Quantification of PD-1 expression in CD8+ CAR+ T cells following a 3-day co-culture with indicated tumor targets. (FIG. 8F) Tumor killing assay comparing PSCA-CAR T cells at 1, 2 or 3-days of co-culture with DU145. PD-1 expression in T cells compared to T cells cultured without tumor targets. (FIG. 8G) Tumor killing assay with different effector:target ratios, assessed by flow cytometry following a 3-day co-culture with PC-3-PSCA or PC-3-PGK100p. Data are shown as n=2 per group±SD. All data are representative of at least two independent experiments.

FIG. 9A-9F: PSCA-BBI CARs show antigen-dependent cytokine production in vitro. (FIG. 9A) IFNγ production quantified by ELISA in supernatants from PSCA-CAR T cells cultured overnight with DU145 or DU145-PSCA tumor cells. (FIG. 9B) Same as in (FIG. 9A) from PSCA-CAR T cells cultured overnight with PC-3, PC-3-PGK100p, or PC-3-PSCA tumor cells. (FIG. 9C) IFNγ production quantified by ELISA in supernatants from PSCA-CAR T cells cultured overnight on plate-bound recombinant human PSCA at varying protein concentrations. (FIG. 9D) Representative zebra plots showing CD107a degranulation by PSCA-CAR T cells following a 4-6 hr co-culture with indicated tumor targets. (FIG. 9E) Quantification of CD107a degranulation by PSCA-CAR T cells from (FIG. 9D). (FIG. 9F) Representative zebra plots of CD137 expression in Mock, PSCA($\Delta$CH2)28$\zeta$, or PSCA($\Delta$CH2)BB$\zeta$ CAR T cells following a 3-day co-culture with indicated tumor targets. Data are shown as n=2 per group±SD. All data are representative of at least two independent experiments.

FIG. 10A-10F: Robust therapeutic efficacy of PSCA ($\Delta$CH2)BB$\zeta$ CAR T cells in subcutaneous and orthotopic bone metastatic human xenograft models of prostate cancer. (FIG. 10A) Tumor volume ($mm^3$) in NSG mice bearing subcutaneous PC-3-PSCA($2.5\times10^6$) tumors on day 0, treated with Mock or PSCA($\Delta$CH2)BB$\zeta$ CAR T cells at the indicated doses by intratumoral (i.t.) injection on day 34. N=4 mice per group. Data are representative of at least two independent experiments. (FIG. 10B) Mice with large tumors (approx. 500 $mm^3$) treated with $5\times10^6$ Mock or CAR T cells by i.v. injection on day 51. N=3 mice per group. Data are representative of at least two independent experiments. (FIG. 10C) Immunohistochemistry of PC-3-PSCA tumors harvested 11 days post i.v. T cell treatment stained with human CD3 (upper panels) and Granzyme B (lower panels). (FIG. 10D) Mice bearing intratibial tumors, with PC-3 (wild-type) cells ($0.2\times10^6$) in the right hind leg, and PC-3-PSCA cells ($0.2\times10^6$) in the left hind leg. On day 14, mice were treated with $5\times10^6$ firefly luciferase-positive (~30%) Mock or PSCA($\Delta$CH2)BB$\zeta$ CAR T cells by i.v. injection. T cell trafficking was monitored at 4 hours, 1 day, 2 days, and 4 days by non-invasive optical imaging (Xenogen). Quantification of flux images, showing the ratio of PC-3-PSCA/ PC-3 (wild-type). N=4-6 mice per group. (FIG. 10E) NSG mice bearing intratibial (left hind leg) PC-3-PSCA-eGFP-ffluc ($0.2\times10^6$). Tumor growth kinetics were monitored by non-invasive optical imaging (Xenogen). On day 14, mice were i.v. injected with $5\times10^6$ Mock or varying doses of PSCA($\Delta$CH2)BB$\zeta$ CAR T cells. Representative flux images of mice on day 13 (pre-treatment) and day 33 are shown. (FIG. 10F) Quantification of flux images (with region of interest (ROI) at site of tumor injection) from tumor only, Mock T cells ($5\times10^6$), and PSCA($\Delta$CH2)BB$\zeta$ CAR T cells ($5\times10^6$, $2.5\times10^6$, $1\times10^6$, $0.5\times10^6$) groups. N 4 mice per group for CAR groups. Data are representative of at least two independent experiments.

FIG. 11A-11D: Durable anti-tumor efficacy of PSCA ($\Delta$CH2)BB$\zeta$ CAR T cells compared with PSCA($\Delta$CH2)28$\zeta$ CAR T cells in a prostate cancer patient-derived bone metastatic xenograft model. (FIG. 11A) NSG mice bearing intratibial (left hind leg) LAPC-9-eGFP-ffluc ($0.15\times10^6$). Tumor growth kinetics were monitored by non-invasive optical imaging (Xenogen). On day 14, mice were i.v. injected with 5×106 Mock, PSCA($\Delta$CH2)28$\zeta$ or PSCA ($\Delta$CH2)BB$\zeta$ CAR T cells. Representative flux images of mice on indicated days are shown. (FIG. 11B) Quantification of flux images, with ROI at the tibia (upper panels) or from whole body (lower panels) from each treatment group. (FIG. 11C) PSA levels determined by ELISA from serum harvested from treated mice (n=2-3 per group) at day 76 post tumor injection. (FIG. 11D) Flow cytometric analysis of peripheral blood of mice 24 and 76 days post tumor injection (n=2-3 per group). Data are compiled from two independent in vivo experiments.

Figure 12:
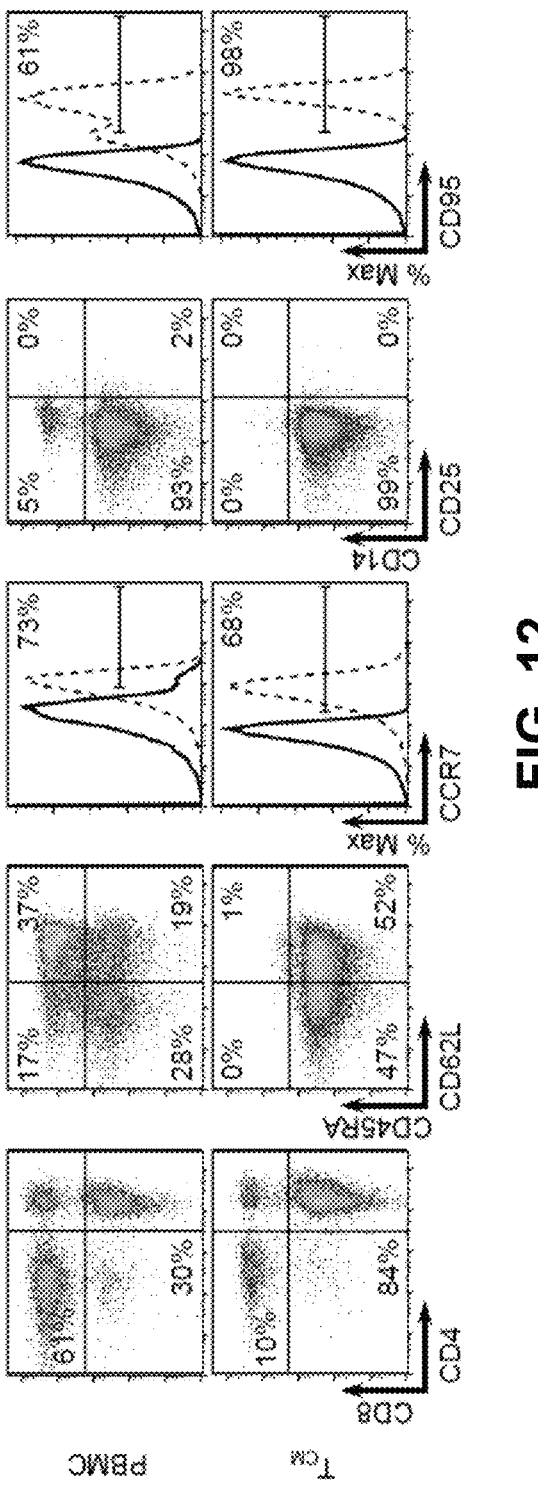

FIG. 12 Cell-surface phenotypes of PBMC and $T_{CM}$ populations. (a) Starting populations of PBMC and TCM were analyzed by flow cytometry for expression of CD4, CD8, CD45RA, CD62L, CCR7, CD14, CD25, and CD95. Representative FACS plots are shown.

Figure 13:
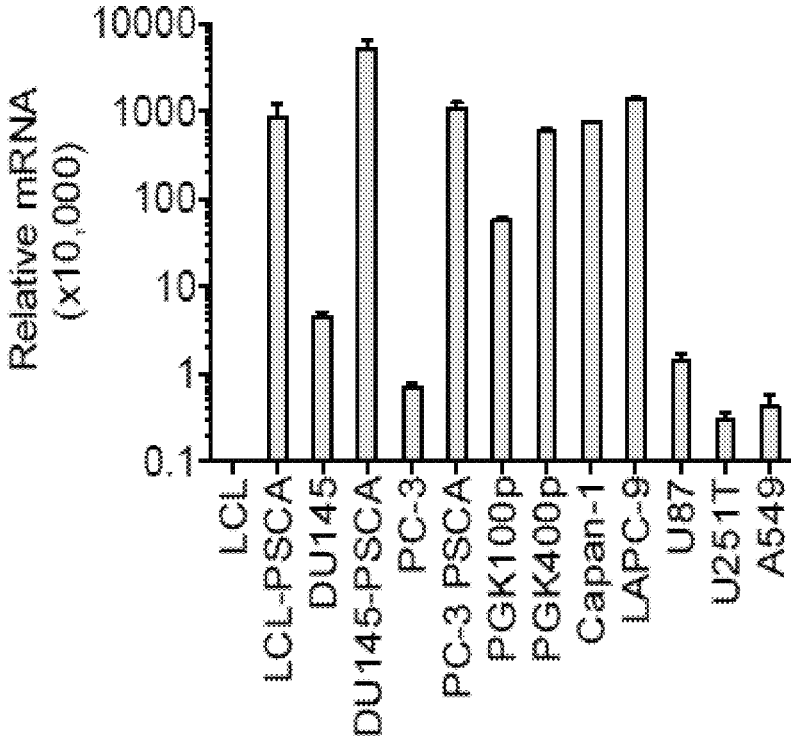

FIG. 13: mRNA expression analysis of PSCA in tumor cell lines. (a) qPCR performed on various prostate and non-prostate cancer cell lines to quantify PSCA expression. PSCA mRNA was normalized to GAPDH mRNA.

Figures 14A, 14B, 14C:
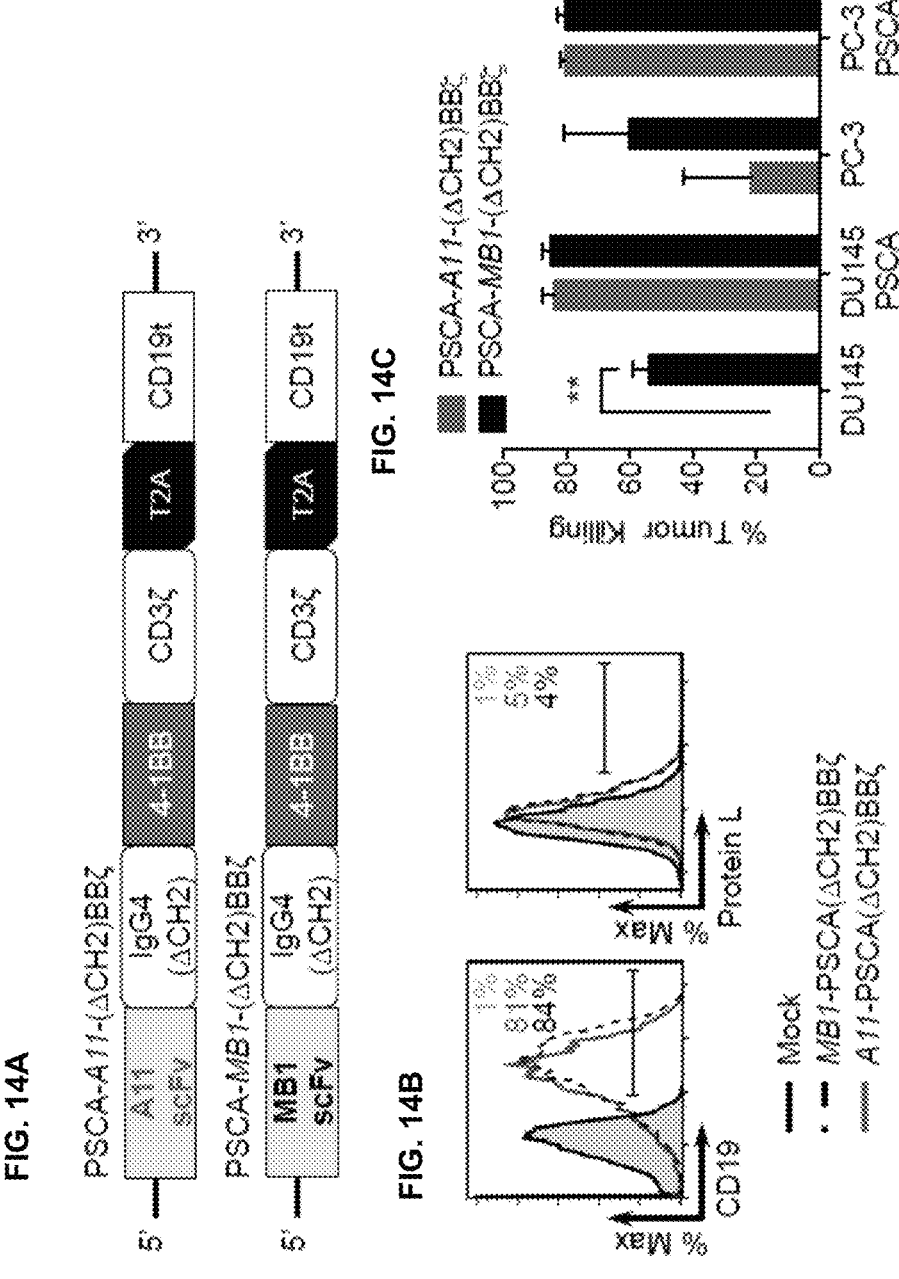

FIG. 14A-14C: Comparison of MB1 scFv-containing and A11 scFv-containing PSCA-CARs. (FIG. 14A) Diagram of the lentiviral expression cassette with PSCA-CARs containing the humanized MB1 or A11 scFv targeting PSCA, with a 129 amino acid modified human IgG4 Fc linker (void of the CH2 domain, $\Delta$CH2), a CD4 transmembrane domain, a cytoplasmic 4-1BB costimulatory domain, and a cytolytic CD3$\zeta$ domain. A truncated non-signaling CD19 (CD19t) is separated from the CAR with a T2A ribosomal skip sequence for tracking CAR-expressing cells. (FIG. 14B) Mock (untransduced), PSCA-MB1-($\Delta$CH2)BB$\zeta$, or PSCA-A11-($\Delta$CH2)BB$\zeta$ CAR T cells expressing CD19 to detect lentiviral transduction of CARs (top) or Protein L to detect the scFv (bottom) as determined by flow cytometry. (FIG. 14C) Tumor killing assay assessed by flow cytometry following a 3-day co-culture with indicated tumor targets.

Figure 15:
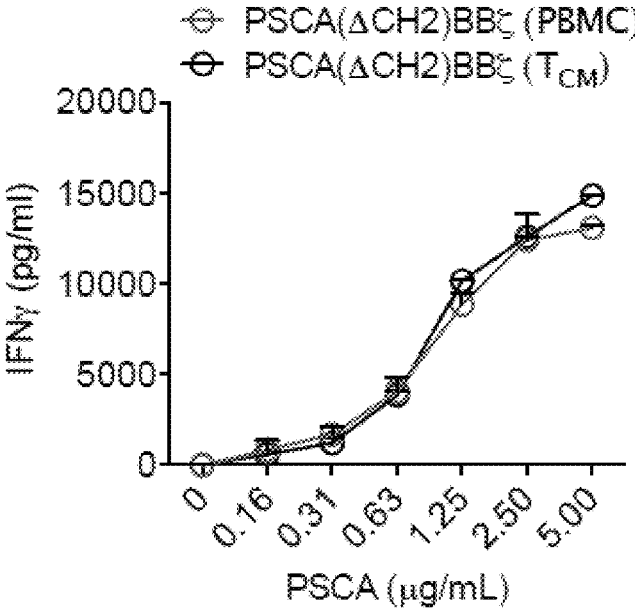

FIG. 15: Cytokine production by PSCA(ΔCH2)BBζ CAR T cells transduced in either PBMC or TCM. IFNγ production quantified by ELISA in supernatants from PSCA-CAR T cells cultured on plate-bound recombinant human PSCA at varying protein concentrations.

Figure 16:
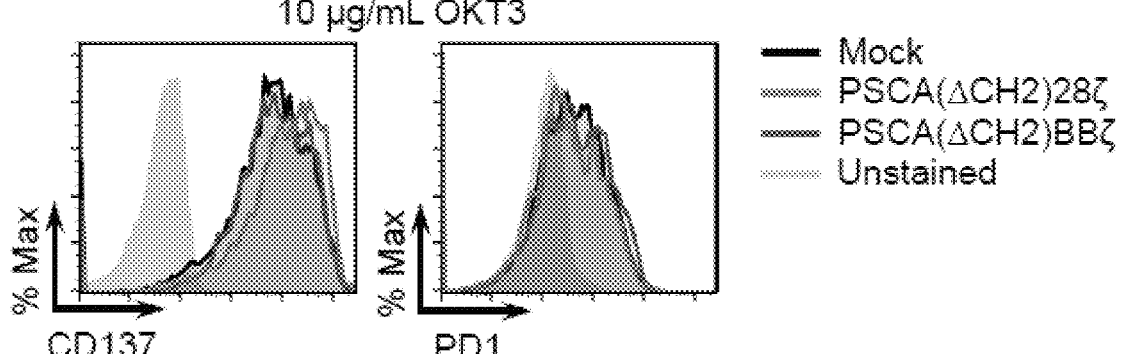

FIG. 16: Activation and exhaustive phenotype of Mock, PSCA(ΔCH2)28ζ, and PSCA(ΔCH2)BBζ CAR T cells against plate-bound OKT3. CD137 and PD1 expression by flow cytometry in T cells following 2-day incubation with plate-bound OKT3 (10 µg/mL).

FIG. 17A-17D: Treatment of PSCA-negative tumor recurrences with HER2-specific CAR T cells. (FIG. 17A) Kinetics of tumor recurrences in PSCA(ΔCH2)BBζ treated PC-3-PSCA tumor bearing mice. Each line represents an individual mouse per group. N=4 per group. Data are representative of at least two independent studies. (FIG. 17B) Immunohistochemistry of PC-3-PSCA tumors harvested from Mock-treated (at primary endpoint) or recurrent PSCA(ΔCH2)BBζ-treated tumors stained with human PSCA, CD3 and HER2. (FIG. 17C) HER2 expression in PC-3-PSCA tumor cells, assessed by flow cytometry. (FIG. 17D) Tumor volume (mm³) in mice bearing PC-3-PSCA tumors treated i.v. with 5×10⁶ Mock or PSCA(ΔCH2)BBζ CAR T cells (N=6 per group) on day 24 ("1st tx"). On day 81, when CAR T cell-treated mice showed tumor recurrence (50-100 mm³), mice were assigned to a second treatment ("2nd tx") receiving i.t. injections of either 5×10⁶ Mock, PSCA(ΔCH2)BBζ, or HER2 CAR T cells (N=2 per group).

FIG. 18: Amino acid sequence of PSCAscFv-IgG4 (HL-CH3)-CD4tm-4IBB-zeta (SEQ ID NO:26).

FIG. 19: Amino acid sequence of PSCAscFv-IgG4 (EQ)-CD28tm-CD28gg-zeta (SEQ ID NO:27).

FIG. 20: Amino acid sequence of PSCAscFv-L-CD4tm-4IBB-zeta (SEQ ID NO: 28).

FIG. 21: Amino acid sequence of PSCAscFv-IgG4 (HL-CH3)-CD28tm-CD28gg-zeta (SEQ ID NO:29).

FIG. 22: Amino acid sequence of PSCAscFv-IgG4 (EQ)-CD4tm-4IBB-zeta (SEQ ID NO:30).

FIG. 23: Amino acid sequence of PSCAscFv-L-CD28tm-4IBB-zeta (SEQ ID NO: 31).

DETAILED DESCRIPTION

Described below is the structure, construction and characterization of various chimeric antigen receptors targeting PSCA. A chimeric antigen (CAR) is a recombinant biomolecule that contains, at a minimum, an extracellular recognition domain, a transmembrane region, and an intracellular signaling domain. The term "antigen," therefore, is not limited to molecules that bind antibodies, but to any molecule that can bind specifically to a target. For example, a CAR can include a ligand that specifically binds a cell surface receptor. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and optionally comprises one or more costimulatory signaling domains. CARs can both to bind antigen and transduce T cell activation, independent of MHC restriction. Thus, CARs are "universal" immunoreceptors which can treat a population of patients with antigen-positive tumors irrespective of their HLA genotype. Adoptive immunotherapy using T lymphocytes that express a tumor-specific CAR can be a powerful therapeutic strategy for the treatment of cancer.

A wide variety of PSCA CAR we generated and tested in several assays to identify a CAR having appropriate activity and specificity while not eliciting excessive cytokine production.

In some cases, the CAR described herein can be produced using a vector in which the CAR open reading frame is followed by a T2A ribosome skip sequence and a truncated CD19 (CD19t), which lacks the cytoplasmic signaling tail (truncated at amino acid 323). In this arrangement, co-expression of CD19t provides an inert, non-immunogenic surface marker that allows for accurate measurement of gene modified cells, and enables positive selection of gene-modified cells, as well as efficient cell tracking and/or imaging of the therapeutic T cells in vivo following adoptive transfer. Co-expression of CD19t provides a marker for immunological targeting of the transduced cells in vivo using clinically available antibodies and/or immunotoxin reagents to selectively delete the therapeutic cells, and thereby functioning as a suicide switch.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient, including unselected PBMC or enriched CD3 T cells or enriched CD3 or memory T cell subsets, can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the Clini-MACS® device to immunomagnetically select cells expressing the desired receptors. The cells enriched for central memory T cells can be activated with anti-CD3/CD28, transduced with, for example, a SIN lentiviral vector that directs the expression of the CAR as well as a truncated human CD19 (CD19t), a non-immunogenic surface marker for both in vivo detection and potential ex vivo selection. The activated/genetically modified central memory T cells can be expanded in vitro with IL-2/IL-15 and then cryopreserved.

Example 1: Construction of CAR Targeting PSCA

FIG. 1 schematically depicts the elements in the open-reading frame of the expression vector used to express the various CAR (upper panel) and the resulting CAR (lower panel). The CAR used the MB1 scFv targeting PSCA. The A11 scFv was not used, but is a suitable alternative. Three different spacers were used: IgG4 (EQ), which includes an IgG4 Fc region, including CH3, CH4 and hinge regions and has two amino acid substitutions that reduce binding to native Fc receptors; IgG4 (HL-CH3), which is similar to IgG4 (EQ), but lacks the CH2 domain and has a short linker sequence located between the hinge region and the CH3 region; and L, which is a short linker sequence. All three spacers are described in detail in Table 1. Two alternative transmembrane domains were used: CD4 and CD28, both described in greater detail in Table 2. Two alternative co-stimulation domains were used: CD28gg, a variant of the CD28 co-stimulatory domain and 4-IBB. Both are described in detail in Table 3. All of the CAR included the CD3ζ cytoplasmic signaling domain, also described in Table 3. The CAR coding sequences were followed by the T2A ribosomal skip sequence and a truncated CD17 sequence to permit co-expression of surface, signaling incompetent, truncated CD19 as a marker.

Bulk central memory T cells that included CD4+ cells and CD8+ cells were transduced with lentivirus expressing one of six different CAR depicted in Table 4. Thus, the CAR included either a 4-IBB co-stimulatory domain (and a CD4 transmembrane domain) or a CD22gg co-stimulatory domain (and a CD28 transmembrane domain) and one of three different spacer domains: IgG4 (EQ), IgG4 (HL-CH3) or L (denoted as EQ, ΔCH2 or L in FIG. 2). FACS was performed to measure T cells expressing CD19 (CD19t) for detection of CAR and Protein L for detection of the scFv to determine stability. The results of this analysis are depicted in FIG. 2.

Example 2: PSCA Expressing Prostate Tumor Cells

Figures 3A, 3B, 3C, 3D, 3E:
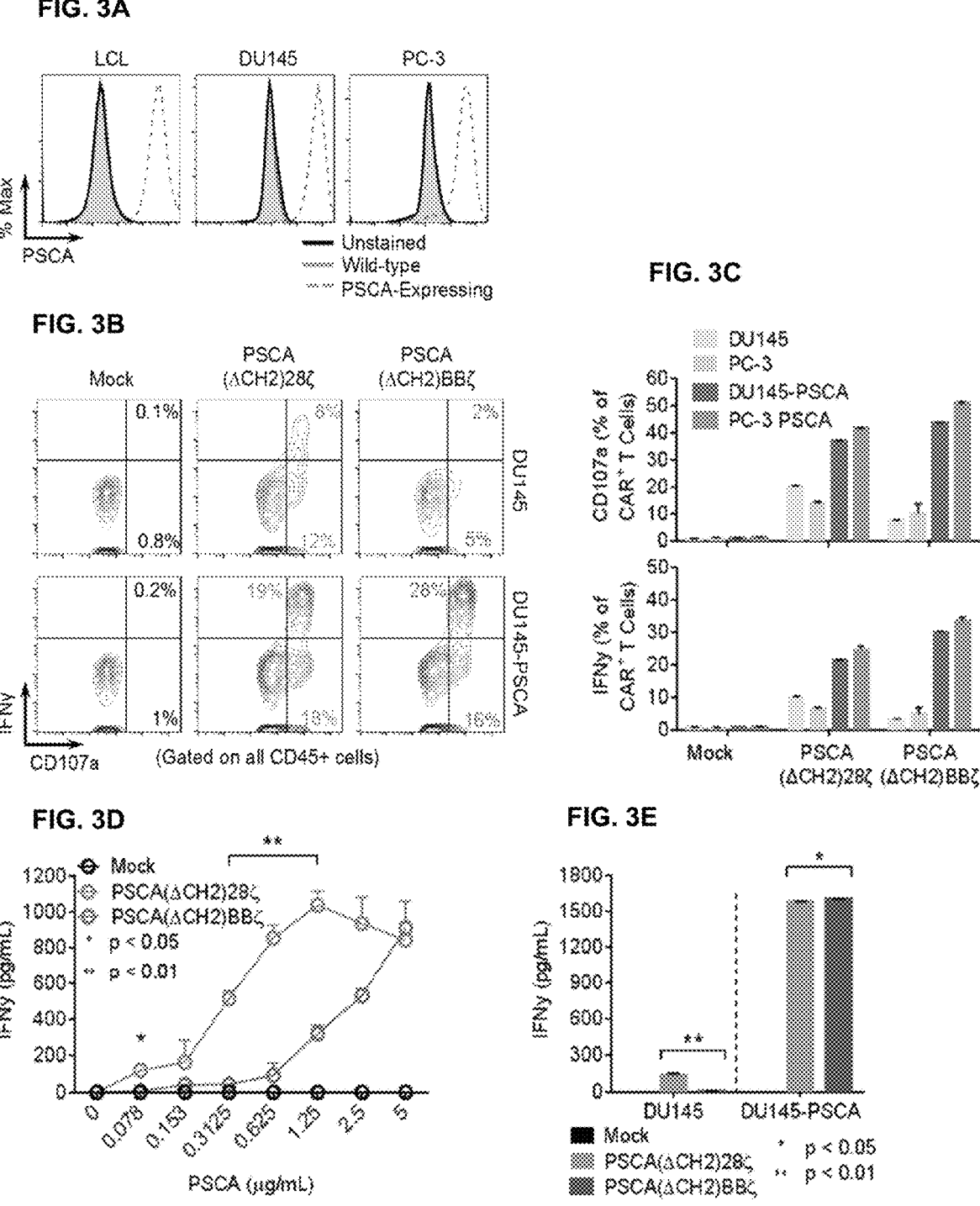

Two different prostate cancer tumor cell lines, PC-3, and DU145, were engineered to express PSCA. FIG. 3A provides PSCA expression data for the parent cells and the engineer cells as well as LCL cells.

Example 3: INF-γ Production by Various PSCA-Targeted T Cells

FIGS. 3B-3E provide IFNγ production data and CD107a degranulation data for the two different CAR following a 5 h co-culture with tumor target (DU145 cells, PC3 cells, DU145 cells transfected with a PSCA expression vector or PC3 cells transfected with a PSCA expression vector), as measured by flow cytometry. FIGS. 4D-4E provide data for IFNγ production by the CAR T cells following a 24 h culture with recombinant PSCA protein or tumor targets, measured by ELISA. Here too it can be seen that CAR with a 4-IBB co-stimulatory domain produce less IFNγ and lower levels of degranulation marker than CAR with a CD28 co-stimulatory domain.

This assessment of degranulation and intracellular IFN-γ production revealed that all CAR that include a CD22gg co-stimulatory domain exhibit non-specific activity against wild-type DU145 cells and wild-type PC3 cells, while CARs that include a 4-IBB co-stimulatory domain exhibit far less non-specific activity. In addition, CAR that include a CD22gg co-stimulatory domain produce more cytokine overall than CARs that include a 4-IBB co-stimulatory domain.

Example 4: Cell Killing by Various CAR

A comparison of a CAR having a CD28 co-stimulatory domain and a CAR having a 4-IBB co-stimulatory domain (described in FIG. 3A) demonstrated that PSCA-CARs containing 4-1BB co-stimulatory domain demonstrate superior specificity, proliferation, and tumor cell killing capacity. The results of this analysis are shown in FIG. 4A-4E. Tumor killing was more specific for CAR having a 4-IBB co-stimulatory domain than a CD28 co-stimulatory domain as shown by the lower killing of cells not transfected with a PSCA expression construct (FIG. 4A). The CAR having a 4-IBB also exhibited lower levels of PD-1 induction (FIG.

4B). Killing and PD-1 induction was measured following a 72 h co-culture with tumor targets (DU145, PC-3, DU145-PSCA, and PC-3-PSCA. FIG. 4C shows the results of an analysis of tumor killing with Effector:Tumor (E:T) ratios from 0.25:1-4:1. FIG. 4D depicts the results of an analysis of proliferation of CAR T cells following a 72 h co-culture with tumor targets and FIG. 4E shows the kinetics of tumor killing and PD-1 induction in CAR T cells following a 1, 2 or 3 day co-culture with tumor targets (DU145, left; DU145-PSCA, right).

Example 5: Impact of Spacer on CAR Function

The studies depicted in FIG. 5A-5B show that the spacer region can impact CD107a expression (degranulation) and IFN-γ production. The CAR here all include a CD4 transmembrane domain and a 4-IBB co-stimulatory domain.

Figures 6A, 6B, 6C, 6D:
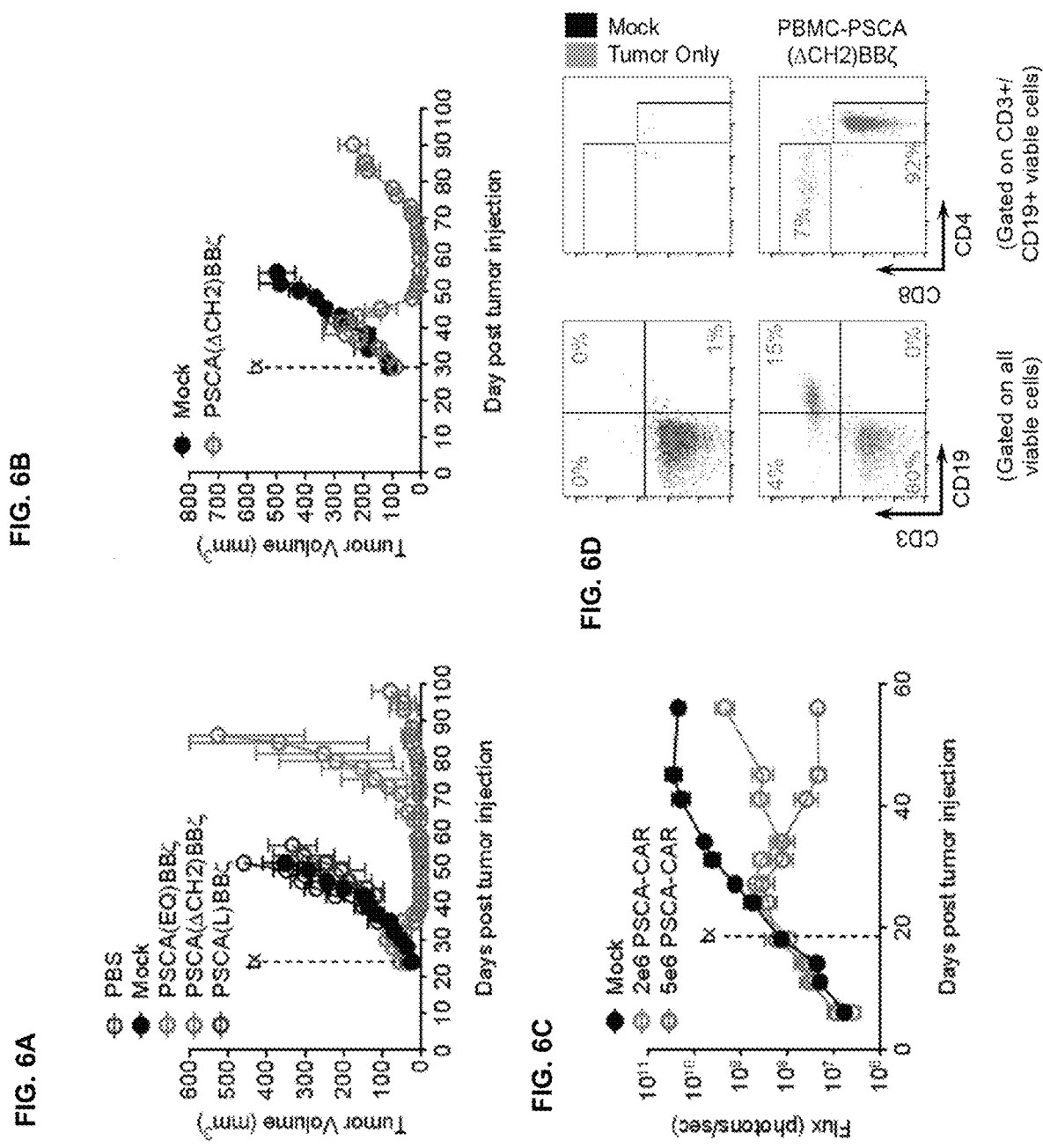

Example 6: Anti-Tumor Efficiency in Prostate Cancer Xenograft and Orthotopic Models Two PSCA-CAR T described above demonstrate potent anti-tumor efficacy in prostate cancer xenograft and orthotopic models. PC-3-PSCA($2\times10^6$) cells were injected subcutaneously in NSG male mice, and when tumors reached ~30-50 mm$^3$, CAR Tcm ($5\times10^6$) were injected intratumorally, and tumor growth was monitored by caliper measurements (FIG. 6A). DU145-PSCA($2\times10^6$) cells were injected subcutaneously in NSG males, and CAR PBMC cells ($5\times10^6$) cells were intravenously delivered (FIG. 6B). To create an orthotopic model, PC-3-PSCA($2\times10^5$) cells were injected intratibially in NSG males, and CAR PBMC cells ($2\times10^6$ or $5\times10^6$) were intravenously delivered (FIG. 6C). CR T cell persistence in blood at 58 days post tumor injection in each group from Panel B was assessed (FIG. 6D).

Figures 7A, 7B, 7C, 7D:
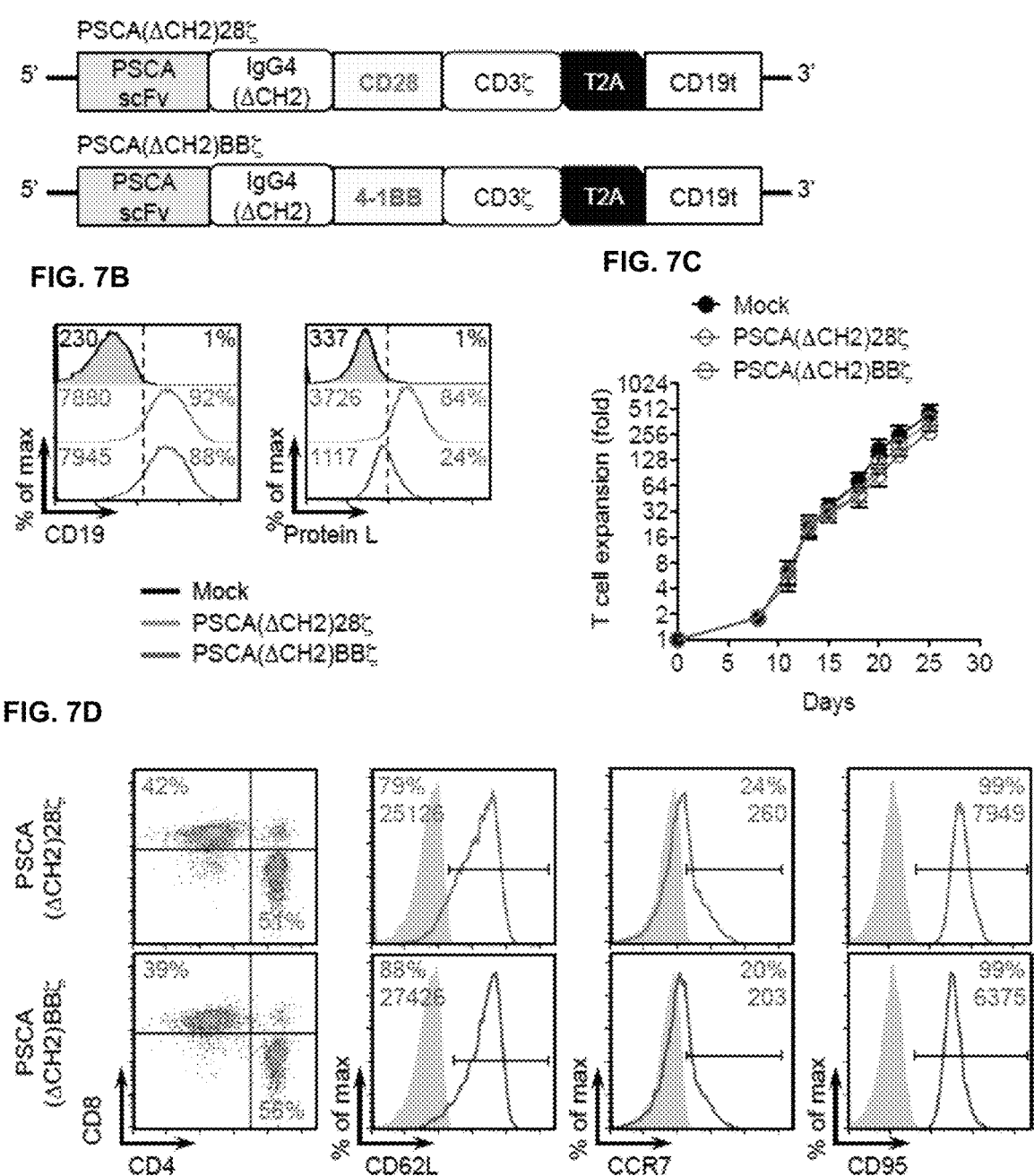

Example 7: PSCA-Targeted CAR Containing 4-1BB Domain Shows Superior Selectivity and Reduce T Cell Exhaustion Compared with a CD28 Domain Two PSCA-CAR constructs that include the humanized PSCA scFv derived from 1G8 (A11 clone) [Lepin et al. 2010 *Eur J Nucl Med Mol Imaging* 37:529), the ΔCH2 extracellular spacer, the CD3ζ cytolytic domain, and the CD19t cell tracker and differ only in their co-stimulatory domain (4-1BB versus CD28 were compared (FIG. 7A). This Example and Examples 8-11 describe studies using PSCA-CARs engineered in PBMC-derived T cells, unless otherwise indicated. For example, central memory T cells (T$_{CM}$)), which have a different starting cell-surface T cell phenotype were used in some studies (FIG. 12).

Both PSCA-CARs were stably expressed (FIG. 7B) as determined by flow cytometric detection of scFv and CD19t, albeit at lower levels for PSCA(ΔCH2)BBζ compared to PSCA(ΔCH2)28ζ. These CAR T cells exhibited comparable ex vivo T cell expansion kinetics (FIG. 7C) and similar cell-surface T cell phenotypes (FIG. 7D).

Next, several human prostate cancer cell lines that were stably engineered to express the human PSCA gene under the control of the EF1α promoter tumor killing abilities of PSCA(ΔCH2)28ζ and PSCA(ΔCH2)BBζ CAR T cells (FIG. 8A). PC-3 tumor cells were also engineered with PSCA driven by a mutant PGK promoter (Frigault et al. 2015 *Cancer Immunol Res* 3:356) to derive a low antigen-density cell line (denoted PGK100p). LAPC-9 is a primary tumor xenograft derived from a patient with bone metastatic prostate cancer (Craft et al. 1999 *Cancer Res* 59:503) that endogenously expresses PSCA. PSCA(ΔCH2)28ζ or PSCA (ΔCH2)BBζ CAR T cells were co-cultured with various tumor targets. Cell imaging demonstrated qualitatively that both CARs killed with similar kinetics (FIG. 8B). In a separate tumor killing assay, flow cytometry was used to quantify tumor killing by PSCA(ΔCH2)28ζ and PSCA (ΔCH2)BBζ CAR T cells. While both PSCA(ΔCH2)28ζ and PSCA(ΔCH2)BBζ CAR T cells killed PSCA-expressing tumor cells with similar efficacy, PSCA(ΔCH2)28ζ showed targeting of wild-type non-PSCA expressing DU145 and PC-3 tumor cells (FIG. 8C). Quantitative real-time PCR analysis of PSCA expression was performed on all tumor targets, and showed that while PSCA protein expression was undetectable by flow cytometry in wild-type DU145 and PC-3 cells, mRNA expression was detected in these lines (FIG. 13), which likely contributed to targeting by CD28-containing CARs.

The impact of an alternative PSCA scFv, MB1 [33], was examined. (FIG. 14A). While both MB1 and A11-based 4-1BB-containing PSCA-CARs were expressed with similar stability (FIG. 14B), CARs containing the MB1 scFv showed significant targeting of wild-type tumor cells compared to CARs containing the A11 scFv (FIG. 14C). These data suggest that antigen-targeting and co-stimulatory domains work in concert to provide tumor selectivity of CARS, and that the non-selectivity of one domain may override the selectivity driven by another domain.

In addition to enhanced selectivity and a lack of killing of wild-type, non-PSCA expressing tumor cells, PSCA(ΔCH2) BBζ CAR T cells exhibited less evidence of exhaustion compared to PSCA(ΔCH2)28ζ CAR T cells, as indicated by reduced expression of programmed death-1 (PD-1) (FIG. 8D). The difference in PD-1 expression between PSCA (ΔCH2)28ζ and PSCA(ΔCH2)BBζ was primarily seen in the CD8+ subset of CAR T cells (FIG. 8E). Additionally, similar trends, albeit less robust, were observed with other exhaustion markers, including LAG3 and TIM3 (data not shown).

A time-course killing assay in which the killing ability of PSCA(ΔCH2)28ζ and PSCA(ΔCH2)BBζ at one, two and three days of co-culture with tumor cells was used to examine the kinetics of PD-1 expression (FIG. 8F). These data quantitatively confirmed that PSCA(ΔCH2)28ζ and PSCA(ΔCH2)BBζ killed DU145-PSCA equivalently over time, but that PSCA(ΔCH2)28ζ had higher PD-1 expression. In another study, PSCA(ΔCH2)28ζ and PSCA(ΔCH2) BBζ were co-cultured against a low PSCA-expressing tumor line (PC-3-PGK100p) and a high PSCA-expressing tumor line (PC-3-PSCA) at varying effector:target (E:T) ratios. This studied showed that at lower E:T ratios, PSCA(ΔCH2) BBζ were more selective for high PSCA-expressing tumor cells compared to PSCA(ΔCH2)28ζ (FIG. 8G). Similar findings were observed using either PBMC- or T$_{CM}$-derived PSCA-CAR T cells (data not shown). Together, these data suggest that 4-1BB co-stimulation allows for potent and selective killing of high PSCA-expressing tumor cells while minimizing activity against lower PSCA-expressing cells, while CD28-containing CARs lack such targeting selectivity.

Example 8:4-1BB-Containing PSCA-CARs Demonstrate Dampened Yet Selective Cytokine Production Compared with CD28-Containing PSCA-CARs To further investigate the differences between CD28- and 4-1BB-containing PSCA-CARs, studies were conducted to compare their respective T cell activation and cytokine production. These studies revealed significant dampening of IFNγ production by PSCA(ΔCH2)BBζ CAR T cells compared to PSCA(ΔCH2)28ζ CAR T cells following an overnight co-culture with DU145-PSCA tumor cells (FIG. 9A). Similar dampening of cytokine production was observed for 4-1BB-containing CARs against PC-3-PSCA. While CD28-containing PSCA-CAR T cells produced equivalent IFNγ levels against low- and high-PSCA-expressing tumor cells, 4-1BB-containing CAR T cells produced lower IFNγ against low PSCA-expressing tumor cells (FIG. 9B). To rule out potential non-CAR-mediated effects on cytokine production by tumor cells, similar IFNγ measurements by PSCA (ΔCH2)BBζ CAR T cells against plate-bound recombinant human PSCA protein were performed. While CD28-containing CAR T cells showed a saturated response against low or high levels of PSCA, IFNγ production by 4-1BB-containing PSCA-CAR T cells was contingent upon antigen density (FIG. 9C). Similar cytokine responses were observed independent of the T cell subset used to generate PSCA-CAR T cells (FIG. 15).

4-1BB-containing PSCA-CARs showed a slight reduction compared to CD28-containing CARs in CD107a degranulation against PSCA-expressing tumor cells (FIG. 9D and FIG. 9E). Significant targeting of non-PSCA-expressing tumor cells by PSCA(ΔCH2)28ζ, as measured by CD107a expression was observed. The activation status of PSCA (ΔCH2)28ζ and PSCA(ΔCH2)BBζ CAR T cells were comparable, as measured by 4-1BB (CD137) expression in a 3-day tumor killing assay (FIG. 9F). To ensure that differences in PSCA-CAR T cells were due to antigen targeting rather than an intrinsic defect in T cell activity, we confirmed similar activation (CD137) and exhaustion (PD-1) in T cells stimulated with plate-bound anti-human CD3 antibody, OKT3 (FIG. 16).

Figures 10A, 10B, 10C, 10D, 10E, 10F:
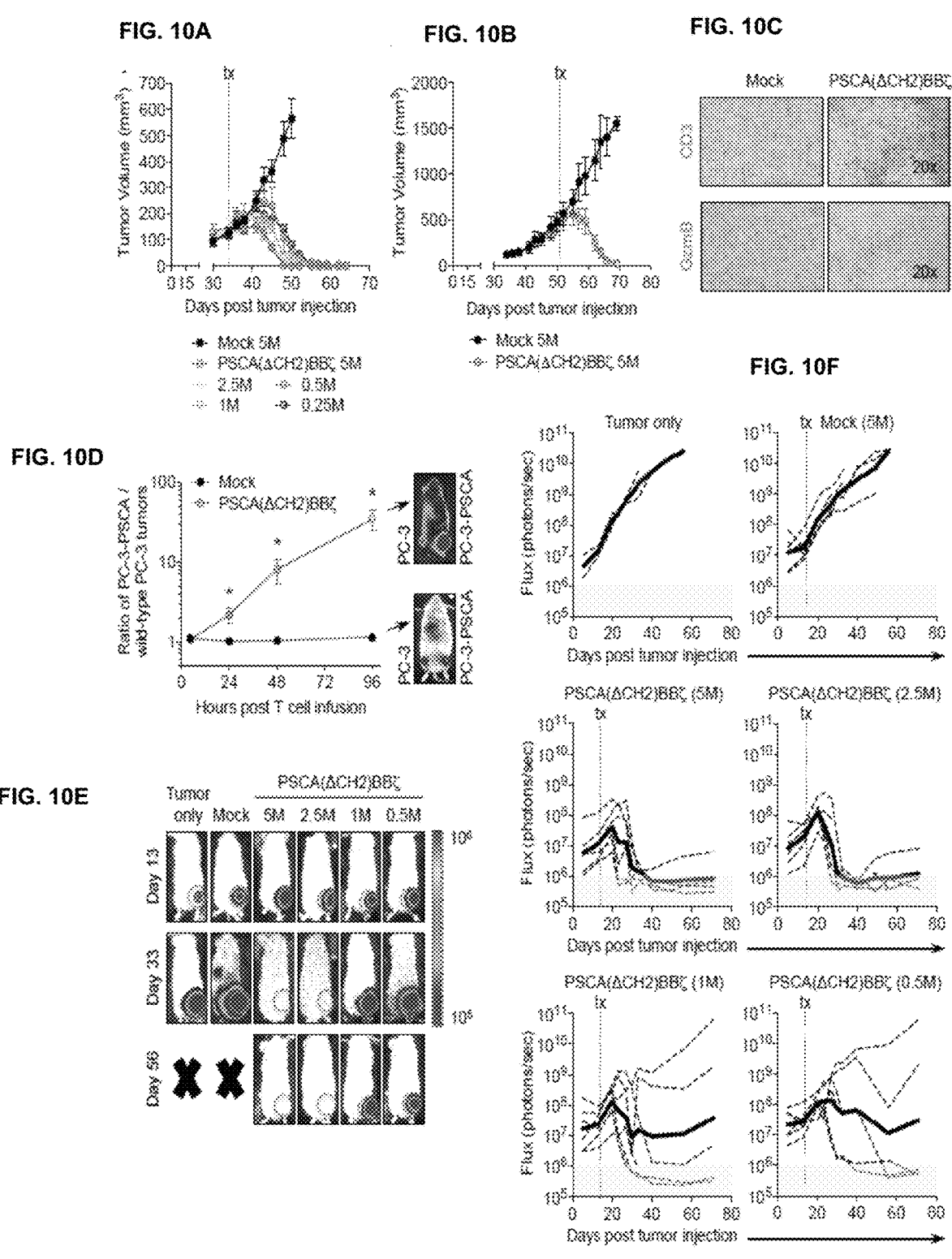

Example 9: PSCA(ΔCH2)BBζ CAR T Cells Demonstrate Robust Therapeutic Efficacy in Subcutaneous Prostate Cancer Models In this study, mice bearing subcutaneous PC-3-PSCA tumors were treated with a single intratumoral injection of $5 \times 10^6$ PSCA(ΔCH2)BBζ CAR T cells. Complete tumor regression was observed within two weeks following intratumoral T cell injection. Although tumor regression was evident for over 30 days, tumors eventually recurred in the majority of animals with similar kinetics as the primary tumor (FIG. 17A), which we will address below. To establish whether systemic therapy of CAR T cells was achievable in this solid tumor model, varying doses of PSCA(ΔCH2)BBζ CAR T cells were delivered intravenously. While $5 \times 10^6$ PSCA-CAR T cells showed complete regression of tumors, a similar yet delayed therapeutic efficacy was observed with a CAR dose as little as $0.25 \times 10^6$ (FIG. 10A). To extend the findings to a large tumor burden, large PC-3-PSCA tumors (~500 mm$^3$) were treated with a single intravenous injection of $5 \times 10^6$ PSCA(ΔCH2)BBζ CAR T cells. Here rapid tumor regression was observed (FIG. 10B). Significant tumor infiltration of human T cells was observed 11 days following CAR T cell infusion (FIG. 10C, upper panel), which also expressed Granzyme B (FIG. 10D, lower panel), a marker of T cell activity. Tumors from Mock-treated mice showed very few human T cells or Granzyme B expression at the same time point.

Figures 17A, 17B, 17C, 17D:
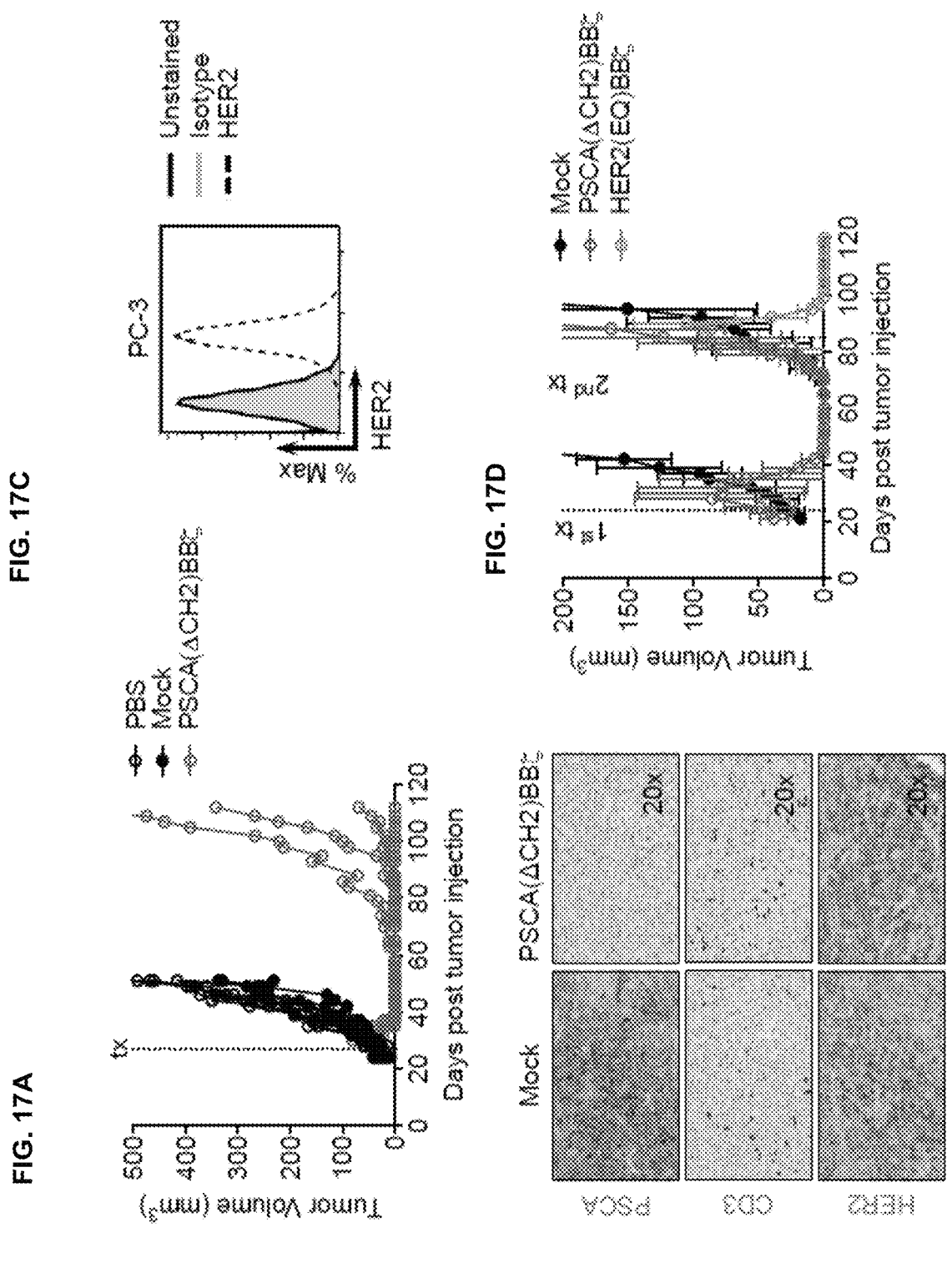

Recurrence following single antigen-specific CAR T cell therapy might be an expected phenomenon given the heterogenic antigen profile of solid tumors, but the mechanisms underlying resistance/recurrence are still being explored. To better understand the delayed tumor recurrences that were observed in FIG. 10A, immunohistochemistry was used to assess the continued presence of antigen on tumor cells, and the PSCA-CAR T cell persistence. Interestingly, while Mock-treated tumors were highly positive for PSCA, tumors that recurred following PSCA(ΔCH2)BBζ CAR T cell treatment were PSCA negative (FIG. 17B, upper panel). In the same recurring tumors, however, human T cells were abundant (FIG. 17B, middle panel), even though these tumors were harvested at least 2-months post-CAR T cell infusion. PC-3 cells also express HER2 in vitro (FIG. 17C) and it was confirmed that both Mock- and PSCA(ΔCH2)BBζ-treated recurrent tumors expressed HER2 at equivalent levels in vivo (FIG. 17B, lower panel). To determine whether tumors were PSCA-negative and still susceptible to CAR T cell therapy, recurrent tumors were treated by intratumoral injection with either Mock, PSCA-directed- or HER2-directed-CAR T cells. Although recurrent PSCA-negative tumors were non-responsive to PSCA-CARs, they were susceptible to HER2-CAR T cell treatment (FIG. 17D).

Example 10: PSCA(ΔCH2)BBζ CAR T Cells Traffic to Bone and Exhibit Anti-Tumor Efficacy in Bone Metastatic Prostate Cancer One of the major obstacles for cellular immunotherapy is the immunosuppressive microenvironment that can hamper effective trafficking and survival of T cells in solid tumors. To directly evaluate trafficking and antigen-dependent CAR T cell expansion in bone metastatic prostate tumors, firefly luciferase-labeled PSCA(ΔCH2)BBζ CAR T cells were i.v. injected into mice bearing intratibial wild-type PC-3 (anatomical right tibia) and PC-3-PSCA (anatomical left tibia) tumors. Interestingly, while Mock and PSCA-CAR T cells showed equal early trafficking to both tumors (at 4 hours post T cell infusion), PSCA-CAR T cells were predominantly found in PSCA-expressing tumors at 1 day following T cell injection, which increased over the 4 days of kinetic imaging (FIG. 10D), indicating antigen-dependent trafficking and/or CAR T cell proliferation in PSCA-positive tumors. Next, a study was conducted in which PC-3-PSCA tumor cells were injected into the intratibial space. On day 14 post tumor engraftment, these tumor-bearing mice were intravenously treated with a dose de-escalation of PSCA (ΔCH2)BBζ CAR T cells ($0.5 \times 10^6$ to $5 \times 10^6$) (FIG. 10E). The large majority of mice treated with either $5 \times 10^6$ or $2.5 \times 10^6$ CAR T cells showed complete tumor regression whereas mice treated with either $1 \times 10^6$ or $0.5 \times 10^6$ CAR T cells had a more heterogeneous therapeutic response (FIG. 10F The clinical relevance of this model is evident when effective doses from the orthotopic studies were compared with doses used in the subcutaneous model where complete regression was observed with CAR T cell doses as little as $0.25 \times 10^6$. It is likely that the discrepancy in overall therapy observed in these models is due to differences in the infiltration and survival of CAR T cells in these tumor microenvironments.

Figure 11A:
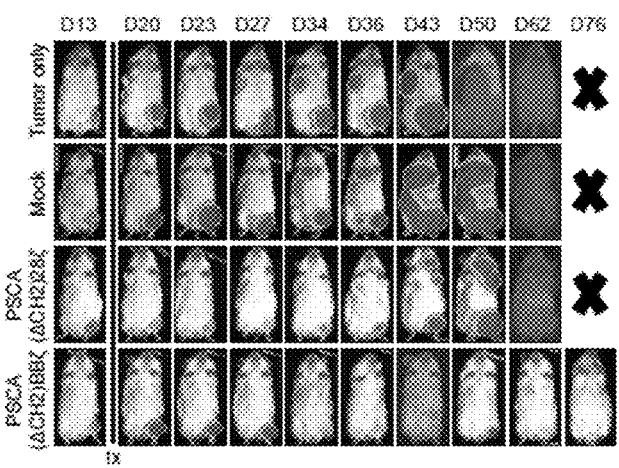

Example 11:4-1BB Co-Stimulation Provides Superior Persistence and Durable Anti-Tumor Responses of PSCA-CARs in a Clinically Relevant Bone Metastatic Prostate Cancer Model The studies described above were extended using the endogenous PSCA-expressing bone metastatic prostate cancer patient-derived tumor xenograft, LAPC-9. On day 14 post tumor engraftment, mice treated with a single i.v. injection of $5 \times 10^6$ PSCA(ΔCH2)BBζ CAR T cells showed near complete regression of tumors at the intratibial tumor site (FIG. 11A). Although intratibial tumors were effectively targeted, LAPC-9 tumors disseminated to other sites in the body, which were found to be particularly evident in various lymph nodes (axillary and inguinal) and the thymus as confirmed by immunohistochemistry (data not shown). Although these seemingly grew for several weeks after initial tumor regression in the bone, they were ultimately eradicated by PSCA(ΔCH2)BBζ CAR T cells.

Figure 11B:
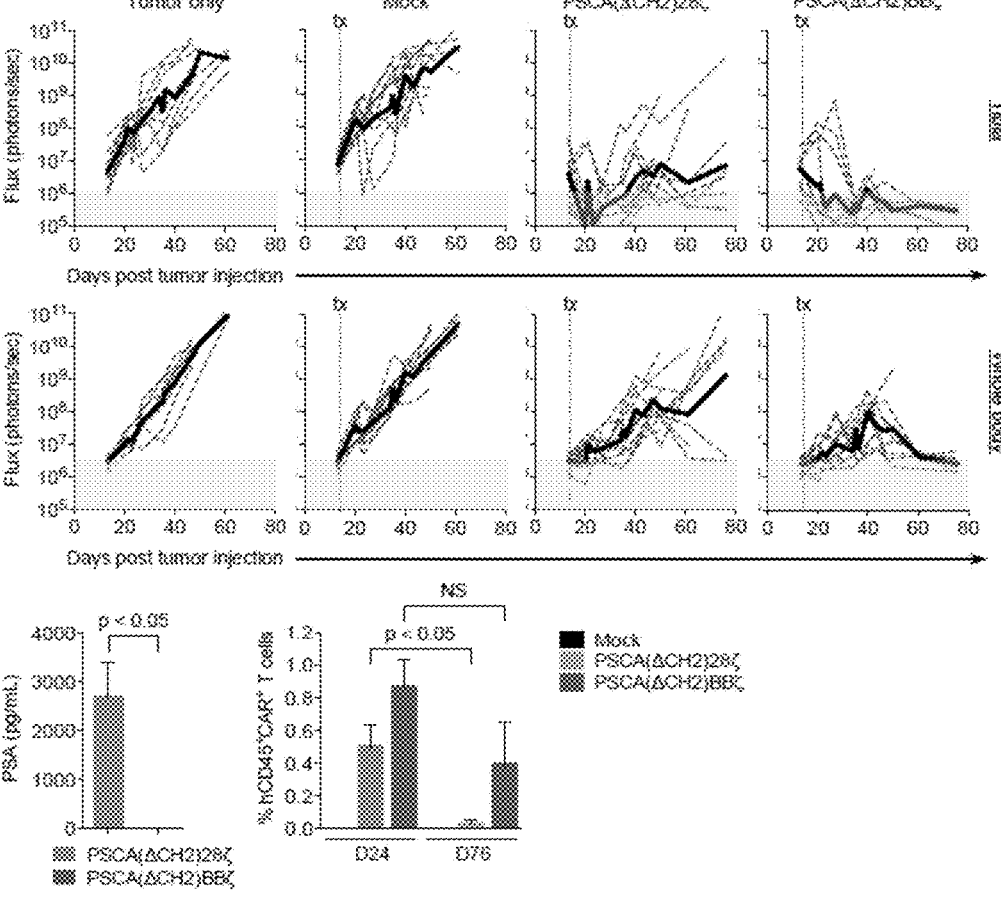

Based on the requirement of persistent T cells for complete anti-tumor activity of PSCA-CARs, a study was conducted to compare PSCA-CARs containing either CD28 or 4-1BB co-stimulatory domains. While both PSCA(ΔCH2) 28ζ and PSCA(ΔCH2)BBζ CAR T cells showed dramatic regression of bone metastases, mice receiving CD28-containing PSCA-CARs showed recurrence at the primary tumor site as well as metastatic disease, while 4-1BB-containing PSCA-CAR-treated mice showed complete anti-tumor responses (FIG. 11A and FIG. 11B). Tumor recurrence in PSCA(ΔCH2)28ζ CAR T cell-treated mice was confirmed by quantifying PSA levels in the blood at Day 76 post CAR T cell treatment (FIG. 10C). CAR T cells were quantified in the blood of treated animals, and while CAR T cells were observed in both groups at Day 24 post tumor injection, PSCA(ΔCH2)BBζ CAR T cells were significantly more abundant at Day 76, indicating greater persistence (FIG. 10D). Overall, these studies demonstrate potent and durable anti-tumor efficacy with PSCA(ΔCH2)BBζ CAR T cells in multiple tumor systems, including orthotopic bone metastatic models of prostate cancer.

Example 12: Construction and Structure of epHIV7 Used for Expression of CAR

The pHIV7 plasmid is the parent plasmid from which the various CAR expression vectors were derived in the T cell Therapeutics Research Laboratory (TCTRL) at City of Hope (COH). The epHIV7 vector used for expression of the CAR was produced from pHIV7 vector. Importantly, this vector uses the human EF1 promoter to drive expression of the CAR. Both the 5' and 3' sequences of the vector were derived from pv653RSN as previously derived from the HXBc2 provirus. The polypurine tract DNA flap sequences (cPPT) were derived from HIV-1 strain pNL4-3 from the NIH AIDS Reagent Repository. The woodchuck post-transcriptional regulatory element (WPRE) sequence was previously described.

Construction of pHIV7 was carried out as follows. Briefly, pv653RSN, containing 653 bp from gag-pol plus 5' and 3' long-terminal repeats (LTRs) with an intervening SL3-neomycin phosphotransferase gene (Neo), was subcloned into pBluescript, as follows: In Step 1, the sequences from 5' LTR to rev-responsive element (RRE) made p5'HIV-1 51, and then the 5' LTR was modified by removing sequences upstream of the TATA box, and ligated first to a CMV enhancer and then to the SV40 origin of replication (p5'HIV-2). In Step 2, after cloning the 3' LTR into pBluescript to make p3'HIV-1, a 400-bp deletion in the 3' LTR enhancer/promoter was made to remove cis-regulatory elements in HIV U3 and form p3'HIV-2. In Step 3, fragments isolated from the p5'HIV-3 and p3'HIV-2 were ligated to make pHIV-3. In Step 4, the p3'HIV-2 was further modified by removing extra upstream HIV sequences to generate p3'HIV-3 and a 600-bp BamHI-SalI fragment containing WPRE was added to p3'HIV-3 to make the p3'HIV-4. In Step 5, the pHIV-3 RRE was reduced in size by PCR and ligated to a 5' fragment from pHIV-3 (not shown) and to the p3'HIV-4, to make pHIV-6. In Step 6, a 190-bp BglII-BamHI fragment containing the cPPT DNA flap sequence from HIV-1 pNL4-3 (55) was amplified from pNL4-3 and placed between the RRE and the WPRE sequences in pHIV6 to make pHIV-7. This parent plasmid pHIV7-GFP (GFP, green fluorescent protein) was used to package the parent vector using a four-plasmid system.

A packaging signal, psi ψ, is required for efficient packaging of viral genome into the vector. The RRE and WPRE enhance the RNA transcript transport and expression of the transgene. The flap sequence, in combination with WPRE, has been demonstrated to enhance the transduction efficiency of lentiviral vector in mammalian cells.

The helper functions, required for production of the viral vector), are divided into three separate plasmids to reduce the probability of generation of replication competent lentivirus via recombination: 1) pCgp encodes the gag/pol protein required for viral vector assembly; 2) pCMV-Rev2 encodes the Rev protein, which acts on the RRE sequence to assist in the transportation of the viral genome for efficient packaging; and 3) pCMV-G encodes the glycoprotein of the vesiculo-stomatitis virus (VSV), which is required for infectivity of the viral vector.

There is minimal DNA sequence homology between the pHIV7 encoded vector genome and the helper plasmids. The regions of homology include a packaging signal region of approximately 600 nucleotides, located in the gag/pol sequence of the pCgp helper plasmid; a CMV promoter sequence in all three helper plasmids; and a RRE sequence in the helper plasmid pCgp. It is highly improbable that replication competent recombinant virus could be generated due to the homology in these regions, as it would require multiple recombination events. Additionally, any resulting recombinants would be missing the functional LTR and tat sequences required for lentiviral replication.

The CMV promoter was replaced by the EF1α-HTLV promoter (EF1p), and the new plasmid was named epHIV7. The EF1p has 563 bp and was introduced into epHIV7 using NruI and NheI, after the CMV promoter was excised.

The lentiviral genome, excluding gag/pol and rev that are necessary for the pathogenicity of the wild-type virus and are required for productive infection of target cells, has been removed from this system. In addition, the CLRX-IgG4Fc (EQ)-CD28-zeta-T2ACD19t_epHIV7 vector construct does not contain an intact 3'LTR promoter, so the resulting expressed and reverse transcribed DNA proviral genome in targeted cells will have inactive LTRs. As a result of this design, no HIV-I derived sequences will be transcribed from the provirus and only the therapeutic sequences will be expressed from their respective promoters. The removal of the LTR promoter activity in the SIN vector is expected to significantly reduce the possibility of unintentional activation of host genes.

Example 13: Production of Vectors for Transduction of T Cells

For each plasmid expressing a CAR, a seed bank was generated, which is used to inoculate the fermenter to produce sufficient quantities of plasmid DNA. The plasmid DNA was tested for identity, sterility and endotoxin prior to its use in producing lentiviral vector.

Briefly, cells were expanded from the 293T working cell (WCB), which has been tested to confirm sterility and the absence of viral contamination. A vial of 293T cells from the 293T WCB was thawed. Cells were grown and expanded until sufficient numbers of cells existed to plate an appropriate number of 10 layer cell factories (CFs) for vector production and cell train maintenance. A single train of cells can be used for production.

The lentiviral vector was produced in sub-batches of up to 10 CFs. Two sub-batches can be produced in the same week leading to the production of approximately 20 L of lentiviral supernatant/week. The material produced from all sub-batches was pooled during the downstream processing phase, in order to produce one lot of product. 293T cells were plated in CFs in 293T medium (DMEM with 10% FBS). Factories were placed in a 37° C. incubator and horizontally leveled in order to get an even distribution of the cells on all the layers of the CF. Two days later, cells were transfected with the four lentiviral plasmids described above using the CaPO₄ method, which involves a mixture of Tris:EDTA, 2M CaCl₂, 2×HBS, and the four DNA plasmids. Day 3 after transfection, the supernatant containing secreted lentiviral vectors was collected, purified and concentrated. After the supernatant was removed from the CFs, End-of-Production Cells were collected from each CF. Cells were trypsinized from each factory and collected by centrifugation. Cells were resuspended in freezing medium and cryopreserved. These cells were later used for replication-competent lentivirus (RCL) testing.

To purify and formulate vectors crude supernatant was clarified by membrane filtration to remove the cell debris. The host cell DNA and residual plasmid DNA were degraded by endonuclease digestion (Benzonase®). The viral supernatant was clarified of cellular debris using a 0.45 μm filter. The clarified supernatant was collected into a pre-weighed container into which the Benzonase® is added (final concentration 50 U/mL). The endonuclease digestion for residual plasmid DNA and host genomic DNA as performed at 37° C. for 6 h. The initial tangential flow ultrafiltration (TFF) concentration of the endonuclease-treated supernatant was used to remove residual low molecular weight components from the crude supernatant, while concentrating the virus ~20 fold. The clarified endonuclease-treated viral supernatant was circulated through a hollow fiber cartridge with a NMWCO of 500 kD at a flow rate designed to maintain the shear rate at ~4,000 sec-1 or less, while maximizing the flux rate. Diafiltration of the nuclease-treated supernatant was initiated during the concentration process to sustain the cartridge performance. An 80% permeate replacement rate was established, using 4% lactose in PBS as the diafiltration buffer. The viral supernatant was brought to the target volume, representing a 20-fold concentration of the crude supernatant, and the diafiltration was continued for 4 additional exchange volumes, with the permeate replacement rate at 100%.

Further concentration of the viral product was accomplished by using a high speed centrifugation technique. Each sub-batch of the lentivirus was pelleted using a Sorvall RC-26 plus centrifuge at 6000 RPM (6,088 RCF) at 6° C. for 16-20 h. The viral pellet from each sub-batch was then reconstituted in a 50 mL volume with 4% lactose in PBS. The reconstituted pellet in this buffer represents the final formulation for the virus preparation. The entire vector concentration process resulted in a 200-fold volume reduction, approximately. Following the completion of all of the sub-batches, the material was then placed at −80° C., while samples from each sub-batch were tested for sterility. Following confirmation of sample sterility, the sub-batches were rapidly thawed at 37° C. with frequent agitation. The material was then pooled and manually aliquoted in the Class II Type A/B3 biosafety cabinet in the viral vector suite. A fill configuration of 1 mL of the concentrated lentivirus in sterile USP class 6, externally threaded O-ring cryovials was used. Center for Applied Technology Development (CATD)'s Quality Systems (QS) at COH released all materials according to the Policies and Standard Operating Procedures for the CBG and in compliance with current Good Manufacturing Practices (cGMPs).

To ensure the purity of the lentiviral vector preparation, it was tested for residual host DNA contaminants, and the transfer of residual host and plasmid DNA. Among other tests, vector identity was evaluated by RT-PCR to ensure that the correct vector is present. All release criteria were met for the vector intended for use in this study.

Example 14: Preparation of T Cells Suitable for Expression of PSCA Targeted CAR T lymphocytes are obtained from a patient by leukopheresis, and the appropriate allogenic or autologous T cell subset, for example, Central Memory T cells ($T_{CM}$), are genetically altered to express the CAR, then administered back to the patient by any clinically acceptable means, to achieve anticancer therapy.

Suitable $T_{CM}$ can be generated as follow. Apheresis products obtained from consented research participants are ficolled, washed and incubated overnight. Cells are then depleted of monocyte, regulatory T cell and naïve T cell populations using GMP grade anti-CD14, anti-CD25 and anti-CD45RA reagents (Miltenyi Biotec) and the Clini-MACS™ separation device. Following depletion, negative fraction cells are enriched for CD62L+ $T_{CM}$ cells using DREG56-biotin (COH clinical grade) and anti-biotin microbeads (Miltenyi Biotec) on the CliniMACS™ separation device.

Following enrichment, $T_{CM}$ cells are formulated in complete X-Vivo15 plus 50 IU/mL IL-2 and 0.5 ng/ml IL-15 and transferred to a Teflon cell culture bag, where they are stimulated with Dynal ClinEx™ Vivo CD3/CD28 beads. Up to five days after stimulation, cells are transduced with lentiviral vector expressing the desired CAR at a multiplicity of infection (MOI) of 1.0 to 0.3. Cultures are maintained for up to 42 days with addition of complete X-Vivo15 and IL-2 and IL-15 cytokine as required for cell expansion (keeping cell density between $3 \times 10^5$ and $2 \times 10^6$ viable cells/mL, and cytokine supplementation every Monday, Wednesday and Friday of culture). Cells typically expand to approximately $10^9$ cells under these conditions within 21 days. At the end of the culture period cells are harvested, washed twice and formulated in clinical grade cryopreservation medium (Cryostore CS5, BioLife Solutions).

On the day(s) of T cell infusion, the cryopreserved and released product is thawed, washed and formulated for re-infusion. The cryopreserved vials containing the released cell product are removed from liquid nitrogen storage, thawed, cooled and washed with a PBS/2% human serum albumin (HSA) Wash Buffer. After centrifugation, the supernatant is removed and the cells resuspended in a Preservative-Free Normal Saline (PFNS)/2% HSA infusion diluent. Samples are removed for quality control testing.

Techniques Used in Examples 7-11

Cell Lines: (Human metastatic prostate cancer cell lines DU145 (ATCC HTB-81) and PC-3 (ATCC CRL-1435) were cultured in RPMI-1640 (Lonza) containing 10% fetal bovine serum (FBS, Hyclone), and 1× antibiotic-antimycotic (Gibco) containing 100 U/mL penicillin, 100 μg/mL streptomycin, and 0.25 ug/mL fungizone (complete RPMI). The human fibrosarcoma cell line, HT1080 (ATCC CCL-121), and the human embryonic kidney cell line, 293T (ATCC CRL-3216), were cultured in Dulbecco's Modified Eagles Medium (DMEM, Life Technologies) containing 10% FBS, 1× antibiotic-antimycotic, 25 mM HEPES (Irvine Scientific), and 2 mM L-Glutamine (Fisher Scientific) (complete DMEM). The human prostate cancer xenograft LAPC-9 (a kind gift from Dr. Robert Reiter, UCLA) was cultured in Iscove's Modified Dulbecco's Medium (IMDM, Irvine Scientific) containing 20% FBS and 1× antibiotic-antimycotic (complete IMDM). LAPC-9 cells were serially passaged in male NOD·Cg-Prkdc$^{scid}$ IL2rg$^{tm1Wjl}$/SzJ (NSG) mice, and single-cell suspensions were prepared as previously described (Craft et al. 1999 *Cancer Res* 59:5030). Briefly, tumor tissue was harvested, minced in a petri dish, and digested with 1% Pronase E (Roche). Following a wash with complete IMDM, single-cell suspensions were filtered through a 40 μm cell strainer (Falcon), washed again, and frozen immediately. An EBV-transformed lymphoblastoid cell line (LCL) and LCL cells containing a membrane-tethered CD3 epsilon specific scFv agonist OKT3 (LCL-OKT3 (Wang et al. 2011 *Blood* 117:1888) were cultured in complete RPMI. All cells were cultured at 37° C. with 5% $CO_2$. DU145 and PC-3 cells were authenticated by STR Profiling and verified *mycoplasma* negative (DDC Medical, OH).

DNA Constructs and Lentivirus Production: DU145 and PC-3 tumor cells were engineered to express PSCA by transduction with epHIV7 lentivirus carrying the human PSCA gene (Accession #: NM_005672.4) under the control of the EF1α promoter. PSCA$^+$ cells were stained with the mouse anti-human PSCA antibody (1G8) as described below (see 'Intracellular/Extracellular Staining and Flow Cytometry' section), and then FACS sorted using the BD FACSAria™ Special Order Research Product (SORP) cell sorter. For generation of tumor cells with low PSCA expression, the PSCA gene was placed under the control of mutated versions of the PGK promoter as previously described (Frigault et al. 2015 *Cancer Immunol Res* 3:356). The A11 scFv (Lepin et al. 2010 *Eur J Nucl Med Mol Imaging* 37:529) sequence was kindly provided by Drs. Anna Wu and Robert Reiter (UCLA). The MB1 scFv sequence was previously published (Feldmann et al. 2012 *J Immunol* 189:3249). CAR constructs with a truncated CD19 gene (CD19t) separated by a T2A ribosomal skip sequence were cloned in an epHIV7 lentiviral backbone. The antigen-targeting domain included either the A11 or the MB1 scFv. The extracellular spacer domain included the 129-amino acid middle-length CH2-deleted version (ΔCH2) of the IgG4 Fc spacer (Jonnalagadda et al. 2015 *Mol Ther* 23:757) intracellular co-stimulatory signaling domain contained that of either CD28 with a CD28 transmembrane domain, or 4-1BB with a CD4 transmembrane domain. The CD3ζ cytolytic domain was previously described (Cooper et al. 2003 *Blood* 101:1637).

Lentivirus was generated by plating 293T cells in T-225 tissue culture flasks 1-day prior to transfection with packaging plasmids and desired CAR lentiviral backbone plasmid. Supernatants were collected after 3 to 4 days, filtered and centrifuged to remove cell debris, and incubated with 2 mM magnesium and 25 U/mL Benzonase® endonuclease (EMD Millipore) to remove contaminating nucleic acids. Supernatants were combined and concentrated via high-speed centrifugation (6080 g) overnight at 4° C. Lentiviral pellets were then resuspended in phosphate-buffered saline (PBS)-lactose solution (4 g lactose per 100 mL PBS), aliquoted and stored at −80° C. for later use. Lentiviral titers, as determined by CD19t expression, were quantified using HT1080 cells.

T Cell Isolation, Lentiviral Transduction, and Ex Vivo Expansion: Leukapheresis products were obtained from consented research participants (healthy donors) under protocols approved by the City of Hope (COH) Internal Review Board (IRB). On the day of leukapheresis, peripheral blood mononuclear cells (PBMC) were isolated by density gradient centrifugation over Ficoll-Paque (GE Healthcare) followed by multiple washes in PBS/EDTA (Miltenyi Biotec). Cells were rested overnight at room temperature (RT) on a rotator, and subsequently washed and resuspended in complete X-VIVO. For studies utilizing total PBMC, cells were immediately frozen in CryoStor® CS5 cryopreservation media (BioLife Solutions). Up to $5\times10^9$ PBMC were incubated with anti-CD14, anti-CD25, and anti-CD45RA microbeads (Miltenyi Biotec) for 30 min at RT and magnetically depleted using the CliniMACS® system (Miltenyi Biotec) according to the manufacturer's protocol. Depleted PBMCs were then enriched for central memory T cells ($T_{CM}$) by incubating with biotinylated anti-CD62L antibody (produced by the Center for Biomedicine and Genetics at City of Hope) for 30 min at RT, and then with anti-Biotin microbeads (Miltenyi Biotec) for an additional 30 min at RT. $T_{CM}$ were then magnetically enriched using the autoMACS® system (Miltenyi Biotec) according to the manufacturer's protocol. For studies utilizing $T_{CM}$, cells were immediately frozen as described above. Purity and phenotype of PBMC and $T_{CM}$ were verified by flow cytometry.

Freshly thawed PBMC or $T_{CM}$ were washed once and cultured in X-VIVO-15 (Lonza) with 10% FBS (complete X-VIVO) containing 100 U/mL recombinant human IL-2 (rhIL-2, Novartis Oncology) and 0.5 ng/mL recombinant human IL-15 (rhIL-15, CellGenix). For CAR lentiviral transduction, T cells were cultured with CD3/CD28 Dynabeads® (Life Technologies), protamine sulfate (APP Pharmaceuticals), cytokine mixture (as stated above) and desired lentivirus at varying MOI either the day of, or the day following, bead stimulation. Spinoculation was performed by centrifugation at 2000 rpm for 30 min at 32° C. with no brake. Cells were then cultured in and replenished with fresh complete X-VIVO containing cytokines every 2-3 days. After 7-9 days, beads were magnetically removed, and cells were further expanded in complete X-VIVO containing cytokines to achieve desired cell yield. CAR T cells were positively selected for CD19t using the EasySep™ CD19 Positive Enrichment Kit I or II (StemCell Technologies) according to the manufacturer's protocol. Following further expansion, cells were frozen prior to in vitro functional assays and in vivo tumor models. Purity and phenotype of CAR T cells were verified by flow cytometry.

Intracellular Extracellular Staining and Flow Cytometry: For flow cytometric analysis, cells were resuspended in FACS buffer (Hank's balanced salt solution without $Ca^{2+}$, $Mg^{2+}$, or phenol red (HBSS$^{-/-}$, Life Technologies) containing 2% FBS and 1× Antibiotic-Antimycotic). For PSCA staining, the mouse anti-human PSCA antibody (1G8) was kindly provided by Dr. Robert Reiter, UCLA. For detecting CAR scFv, biotinylated Protein-L (GenScript USA) was used as previously described[35]. Cells were incubated with primary antibodies for 30 minutes at 4° C. in the dark before proceeding to secondary staining. For extracellular and secondary staining, cells were washed twice prior to 30 min incubation at 4° C. in the dark with fluorescein isothiocyanate (FITC), phycoerythrin (PE), peridinin chlorophyll protein complex (PerCP), PerCP-Cy5.5, PE-Cy7, allophycocyanin (APC), and APC-Cy7 (or APC-eFluor780)-conjugated antibodies (CD3, CD4, CD8, CD14, CD19, CD25, mouse- or human-specific CD45, CD45RA, CD45RO, CD62L, CD95, CD107a, CD137, LAG3 (CD223), PD-1 (CD279), TIM3 (CD366), CCR7, IFNγ, Goat Anti-Mouse Ig, and streptavidin) purchased from BioLegend, eBioscience, BD Biosciences or Fisher Scientific. Cell viability was determined using 4', 6-diamidino-2-phenylindole (DAPI, Sigma). For intracellular staining, cells were fixed, permeabilized, and processed according to the PE Active-Caspase-3 Apoptosis kit (BD Biosciences) manufacturer's protocol. Cells were then incubated with fluorophore-conjugated antibodies for 30 minutes at 4° C. in the dark, and washed twice prior to resuspension in FACS buffer and acquisition on the MACSQuant Analyzer 10 (Miltenyi Biotec). Data were analyzed with FlowJo software (v10, TreeStar).

In Vitro T Cell Functional Assays: For degranulation and intracellular cytokine assays, CAR T cells and tumor targets were co-cultured at varying effector:target ratios in complete X-VIVO without exogenous cytokines in round-bottom 96-well tissue culture-treated plates (Corning). FITC-CD107a was added to cultures and after incubating for 4-6 hrs at 37° C., cells were fixed and permeabilized before analysis by flow cytometry as described above. For tumor killing assays, CAR T cells and tumor targets were co-cultured at varying effector:target ratios in complete X-VIVO without exogenous cytokines in 96-well plates for 1-5 days and analyzed by flow cytometry as described above. Tumor killing by CAR T cells was calculated by comparing CD45-negative cell counts relative to that observed by Mock T cells.

ELISA and Multiplex Cytokine Assays: Varying concentrations of recombinant human PSCA protein (amino acids 23-95; Abnova) was coated overnight in 1×PBS at 4° C. on high-affinity 96-well flat bottom plates (Corning). Wells were washed twice with 1×PBS, blocked with 10% FBS for 1 hr, and washed again. CAR T cells ($5\times10^3$ in 200 μL) were added to coated wells. Where specified, tumor targets ($5\times10^3$) were incubated with T cells in non-coated wells (final volume of 200 μL). Following an overnight incubation at 37° C.), supernatants were harvested and processed according to the Human IFNγ ELISA Ready-SET-GO!® (eBioscience) manufacturer's protocol. Plates were read at 450 nm using the Wallac Victor3 1420 Multilabel Counter (Perkin-Elmer) and Wallac 1420 Workstation software. Alternatively, supernatants were analyzed for multiple cytokines using the Multiplex Bead Immunoassay Kit (Invitrogen) according to the manufacturer's protocol. Human PSA/KLK3 ELISA (Abcam) on mouse serum was run according to manufacturer's protocol.

Quantitative PCR: Tumor cells (plated at $0.25\times10^6$/mL) were cultured for one day prior to RNA isolation. RNA was extracted using RNeasy® Mini Kit column purification (Qiagen). cDNA was prepared using SuperScript™ IV First-Strand Synthesis System (Invitrogen). RNA primers were generated using TaqMan® Gene Expression Assays specific to either PSCA(Hs04166224_g1, Life Technologies) or GAPDH (Hs02758991_g1, Life Technologies). qPCR was performed on a ViiA™ 7 Real-Time PCR System (Thermo Fisher). Primer sets were validated using a standard curve across a specified dynamic range with a single melting curve peak. Expression of target genes was normalized to GAPDH.

In Vivo Tumor Studies: All animal experiments were performed under protocols approved by the City of Hope Institutional Animal Care and Use Committee. For subcu-
taneous tumor studies, PC-3 and DU145 cells ($2.5 \times 10^6$)
were prepared in HBSS$^{-/-}$ and injected subcutaneously in
the left depilated belly of male NSG mice. Tumor growth
was monitored 3 times per week via caliper measurement.
Once tumor volumes reached 50-500 mm³, CAR T-cells
were prepared in PBS and injected either intratumorally (i.t.)
or intravenously (i.v.). Once tumors reached 15 mm in
diameter, mice were euthanized and tumors were harvested
and processed for immunohistochemistry as described
below. When subcutaneous tumors recurred, mice were
treated by i.t. injection with either PSCA-CARs or HER2-
CARs. Peripheral blood was collected from isoflurane-
anesthetized mice by retro-orbital (RO) bleed through hepa-
rinized capillary tubes (Chase Scientific) and into
polystyrene tubes containing a heparin/PBS solution (1000
units/mL, Sagent Pharmaceuticals). Approximately 150 μL
of blood was collected per mouse. Blood was lysed with 1×
Red Cell Lysis Buffer (Sigma) according to the manufac-
turer's protocol, and then washed, stained and analyzed by
flow cytometry as described above.

For orthotopic intratibial tumor studies, LAPC-9 and
PC-3-PSCA were transduced with lentivirus carrying
enhanced green fluorescent protein (eGFP)/firefly luciferase
(ffluc) to allow for non-invasive optical imaging (Xenogen)
once implanted into mice (resulting lines named LAPC-9-
eGFP-ffluc and PC-3-PSCA-eGFP-ffluc). Briefly, these lines
were incubated with polybrene (4 mg/mL, Sigma) and the
eGFP-ffluc lentivirus (see above), followed by cell sorting
for GFP$^+$ cells using the BD FACSAria™ SORP cell sorter.
Freshly sorted LAPC-9-eGFP-ffluc cells were serially pas-
saged in NSG mice as described above. PC-3-PSCA-eGFP-
ffluc cells ($2 \times 10^5$) or LAPC-9-eGFP-ffluc cells ($1.5 \times 10^5$)
were prepared as in subcutaneous models. Mice were anes-
thetized by intraperitoneal (i.p.) injection of ketamine/xylazine and gaseous isoflurane prior to tumor injection. Tumor
cells (in 30 μL HBSS$^{-/-}$) were injected in the intratibial
space of the mouse hind leg. After 14 days, mice were i.v.
injected with CAR T cells. Tumor growth was monitored via
biweekly optical imaging (IVIS, Xenogen) and flux signals
were analyzed with Living Image software (Xenogen). For
imaging, mice were injected i.p. with 150 μL D-luciferin
potassium salt (Perkin Elmer) suspended in PBS at 4.29
mg/mouse.

For T cell trafficking studies, mice were implanted in the
right intratibial space with wild-type PC-3 cells ($2 \times 10^5$) and
in the left intratibial space with PC-3-PSCA cells ($2 \times 10^5$).
After 14 days, mice were i.v. injected with $5 \times 10^6$ Mock or
PSCA(ΔCH2)BBζ CAR T cells that had been co-transduced
with lentivirus carrying eGFP-ffluc. T cells were CAR
enriched, and determined to be approximately 30% eGFP$^+$
by flow cytometry. T cell trafficking was monitored by
non-invasive optical imaging (Xenogen) at 4 hr, 1 day, 2
days, and 4 days post T cell infusion. Flux signals were
analyzed as described above.

Immunohistochemistry: Tumor tissue was fixed for up to
3 days in 4% paraformaldehyde (Boston BioProducts) and
stored in 70% ethanol until further processing. Histology
was performed by the Pathology Core at City of Hope.
Briefly, paraffin-embedded sections (10-μm) were stained
with mouse anti-human CD3 (DAKO), mouse anti-human
PSCA(Abcam), rat anti-human HER2 (DAKO), and rat
anti-human Granzyme-B (eBioscience). Images were
obtained using the Nanozoomer 2.0HT digital slide scanner
and the associated NDP.view2 software (Hamamatzu).

Statistical Analysis: Data are presented as mean±SEM,
unless otherwise stated. Statistical comparisons between
groups were performed using the unpaired two-tailed Stu-
dent's t test to calculate p value. *p<0.05, **p<0.01,
***p<0.001; ns, not significant.

What is claimed is:

1. A nucleic acid molecule encoding a chimeric antigen receptor (CAR) selected from the group consisting of:
   (a) a CAR comprising a Prostate Stem Cell Antigen (PSCA) scFV comprising the amino acid sequence of SEQ ID NO: 38, a spacer comprising the amino acid sequence of SEQ ID NO: 9, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21;
   (b) a CAR comprising a PSCA scFV comprising the amino acid sequence of SEQ ID NO: 38, a spacer comprising the amino acid sequence of SEQ ID NO: 2, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21; or
   (c) a CAR comprising a PSCA scFV comprising the amino acid sequence of SEQ ID NO: 38, a spacer comprising the amino acid sequence of SEQ ID NO: 10, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

2. The nucleic acid molecule of claim 1, wherein the CAR comprises: PSCA scFV comprising the amino acid sequence of SEQ ID NO: 38, a spacer comprising the amino acid sequence of SEQ ID NO: 9, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

3. The nucleic acid molecule of claim 1, wherein the CAR comprises: a PSCA scFV comprising the amino acid sequence of SEQ ID NO: 38, a spacer comprising the amino acid sequence of SEQ ID NO: 2, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

4. The nucleic acid molecule of claim 1, wherein the CAR comprises: a PSCA scFV comprising the amino acid sequence of SEQ ID NO: 38, a spacer comprising the amino acid sequence of SEQ ID NO: 10, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

5. A population of human T cells comprising a nucleic acid encoding a CAR selected from the group consisting of:
   (a) a CAR comprising a PSCA scFV comprising the amino acid sequence of SEQ ID NO: 38, a spacer comprising the amino acid sequence of SEQ ID NO: 9, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21;

(b) a CAR comprising a PSCA scFV comprising the amino acid sequence of SEQ ID NO: 38, a spacer comprising the amino acid sequence of SEQ ID NO: 2, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21; or (c) a CAR comprising a PSCA scFV comprising the amino acid sequence of SEQ ID NO: 38, a spacer comprising the amino acid sequence of SEQ ID NO: 10, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

6. The population of human T cells of claim 5, wherein the CAR comprises: PSCA scFV comprising the amino acid sequence of SEQ ID NO: 38, a spacer comprising the amino acid sequence of SEQ ID NO: 9, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

7. The population of human T cells of claim 5, wherein the CAR comprises: a PSCA scFV comprising the amino acid sequence of SEQ ID NO: 38, a spacer comprising the amino acid sequence of SEQ ID NO: 2, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

8. The population of human T cells of claim 5, wherein the CAR comprises: a PSCA scFV comprising the amino acid sequence of SEQ ID NO: 38, a spacer comprising the amino acid sequence of SEQ ID NO: 10, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

9. The population of human T cells of claim 5, wherein the population of T cells comprises central memory T cells.

10. A CAR selected from the group consisting of:

(a) a CAR comprising a PSCA scFV comprising the amino acid sequence of SEQ ID NO: 38, a spacer comprising the amino acid sequence of SEQ ID NO: 9, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21;

(b) a CAR comprising a PSCA scFV comprising the amino acid sequence of SEQ ID NO: 38, a spacer comprising the amino acid sequence of SEQ ID NO: 2, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21; or (c) a CAR comprising a PSCA scFV comprising the amino acid sequence of SEQ ID NO: 38, a spacer comprising the amino acid sequence of SEQ ID NO: 10 a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

11. The CAR of claim 10, wherein the CAR comprises: PSCA scFV comprising the amino acid sequence of SEQ ID NO: 38, a spacer comprising the amino acid sequence of SEQ ID NO: 9, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

12. The CAR of claim 10, wherein the CAR comprises: a PSCA scFV comprising the amino acid sequence of SEQ ID NO: 38, a spacer comprising the amino acid sequence of SEQ ID NO: 2, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

13. The CAR of claim 10, wherein the CAR comprises: a PSCA scFV comprising the amino acid sequence of SEQ ID NO: 38, a spacer comprising the amino acid sequence of SEQ ID NO: 10, a CD4 transmembrane domain comprising the amino acid sequence of SEQ ID NO: 16, a 41-BB co-stimulatory domain comprising the amino acid sequence of SEQ ID NO: 24, and CD3ζ domain comprising the amino acid sequence of SEQ ID NO: 21.

14. A method for treating a human patient having a cancer expressing PSCA, the method comprising administering to the patient the population of human T cells of claim 5.

15. The method of claim 14, wherein the population of human T cells are allogeneic to the patient.

16. The method of claim 15, wherein the cancer is prostate cancer.

17. The method of claim 15, wherein the cancer is a bone metastasis of prostate cancer.

18. The method of claim 15, wherein the cancer is pancreatic cancer.

19. The method of claim 15, wherein the CAR comprises an amino acid sequence selected from SEQ ID NOs: 26, 28, 30, 32, 34, and 36.

* * * * *

```
SEQUENCE LISTING

Sequence total quantity: 38
SEQ ID NO: 1          moltype = AA  length = 236
FEATURE               Location/Qualifiers
REGION                1..236
                      note = an scFv directed against PSCA
source                1..236
                      mol_type = protein
                      organism = synthetic construct
SEQUENCE: 1
DIQLTQSPST LSASVGDRVT ITCSASSSVR FIHWYQQKPG KAPKRLIYDT SKLASGVPSR  60
FSGSGSGTDF TLTISSLQPE DFATYYCQQW GSSPFTFGQG TKVEIKGSTS GGGSGGGSGG  120
GGSSEVQLVE YGGGLVQPGG SLRLSCAASG FNIKDYYIHW VRQAPGKGLE WVAWIDPENG  180
DTEFVPKFQG RATMSADTSK NTAYLQMNSL RAEDTAVYYC KTGGFWGQGT LVTVSS      236

SEQ ID NO: 2          moltype = AA  length = 10
FEATURE               Location/Qualifiers
source                1..10
                      mol_type = protein
                      note = linker
                      organism = synthetic construct
SEQUENCE: 2
GGGSSGGGSG                                                         10

SEQ ID NO: 3          moltype = AA  length = 12
FEATURE               Location/Qualifiers
REGION                1..12
                      note = mutated sequence - based on human IgG4 hinge
source                1..12
                      mol_type = protein
                      organism = synthetic construct
SEQUENCE: 3
ESKYGPPCPP CP                                                      12
```

-continued

```
SEQ ID NO: 4              moltype = AA   length = 12
FEATURE                   Location/Qualifiers
source                    1..12
                          mol_type = protein
                          organism = Homo sapiens
SEQUENCE: 4
ESKYGPPCPS CP                                                          12

SEQ ID NO: 5              moltype = AA   length = 20
FEATURE                   Location/Qualifiers
REGION                    1..20
                          note = human IgG4 hinge and linker sequence
source                    1..20
                          mol_type = protein
                          organism = synthetic construct
SEQUENCE: 5
ESKYGPPCPP CPGGGSSGGG                                                  20

SEQ ID NO: 6              moltype = AA   length = 39
FEATURE                   Location/Qualifiers
source                    1..39
                          mol_type = protein
                          organism = Homo sapiens
SEQUENCE: 6
IEVMYPPPYL DNEKSNGTII HVKGKHLCPS PLFPGPSKP                             39

SEQ ID NO: 7              moltype = AA   length = 48
FEATURE                   Location/Qualifiers
source                    1..48
                          mol_type = protein
                          organism = Homo sapiens
SEQUENCE: 7
AKPTTTPAPR PPTPAPTIAS QPLSLRPEAC RPAAGGAVHT RGLDFACD                   48

SEQ ID NO: 8              moltype = AA   length = 45
FEATURE                   Location/Qualifiers
source                    1..45
                          mol_type = protein
                          organism = Homo sapiens
SEQUENCE: 8
TTTPAPRPPT PAPTIASQPL SLRPEACRPA AGGAVHTRGL DFACD                      45

SEQ ID NO: 9              moltype = AA   length = 129
FEATURE                   Location/Qualifiers
REGION                    1..129
                          note = fusion of hinge-linker-CH3 /IgG4 HL-CH3
source                    1..129
                          mol_type = protein
                          organism = synthetic construct
SEQUENCE: 9
ESKYGPPCPP CPGGGSSGGG SGGQPREPQV YTLPPSQEEM TKNQVSLTCL VKGFYPSDIA      60
VEWESNGQPE NNYKTTPPVL DSDGSFFLYS RLTVDKSRWQ EGNVFSCSVM HEALHNHYTQ      120
KSLSLSLGK                                                              129

SEQ ID NO: 10             moltype = AA   length = 229
FEATURE                   Location/Qualifiers
REGION                    1..229
                          note = fusion with mutations
source                    1..229
                          mol_type = protein
                          organism = synthetic construct
SEQUENCE: 10
ESKYGPPCPP CPAPEFEGGP SVFLFPPKPK DTLMISRTPE VTCVVVDVSQ EDPEVQFNWY      60
VDGVEVHNAK TKPREEQFQS TYRVVSVLTV LHQDWLNGKE YKCKVSNKGL PSSIEKTISK      120
AKGQPREPQV YTLPPSQEEM TKNQVSLTCL VKGFYPSDIA VEWESNGQPE NNYKTTPPVL      180
DSDGSFFLYS RLTVDKSRWQ EGNVFSCSVM HEALHNHYTQ KSLSLSLGK                  229

SEQ ID NO: 11             moltype =    length =
SEQUENCE: 11
000

SEQ ID NO: 12             moltype = AA   length = 107
FEATURE                   Location/Qualifiers
source                    1..107
                          mol_type = protein
                          organism = Homo sapiens
SEQUENCE: 12
GQPREPQVYT LPPSQEEMTK NQVSLTCLVK GFYPSDIAVE WESNGQPENN YKTTPPVLDS      60
DGSFFLYSRL TVDKSRWQEG NVFSCSVMHE ALHNHYTQKS LSLSLGK                    107
```

```
SEQ ID NO: 13            moltype = AA  length = 21
FEATURE                  Location/Qualifiers
source                   1..21
                         mol_type = protein
                         organism = Homo sapiens
SEQUENCE: 13
LCYLLDGILF IYGVILTALF L                                          21

SEQ ID NO: 14            moltype = AA  length = 27
FEATURE                  Location/Qualifiers
source                   1..27
                         mol_type = protein
                         organism = Homo sapiens
SEQUENCE: 14
FWVLVVVGGV LACYSLLVTV AFIIFWV                                    27

SEQ ID NO: 15            moltype = AA  length = 28
FEATURE                  Location/Qualifiers
source                   1..28
                         mol_type = protein
                         organism = Homo sapiens
SEQUENCE: 15
MFWVLVVVGG VLACYSLLVT VAFIIFWV                                   28

SEQ ID NO: 16            moltype = AA  length = 22
FEATURE                  Location/Qualifiers
source                   1..22
                         mol_type = protein
                         organism = Homo sapiens
SEQUENCE: 16
MALIVLGGVA GLLLFIGLGI FF                                         22

SEQ ID NO: 17            moltype = AA  length = 21
FEATURE                  Location/Qualifiers
REGION                   1..21
                         note = transmembrane domain, CD8tm
source                   1..21
                         mol_type = protein
                         organism = synthetic construct
SEQUENCE: 17
IYIWAPLAGT CGVLLLSLVI T                                          21

SEQ ID NO: 18            moltype = AA  length = 23
FEATURE                  Location/Qualifiers
REGION                   1..23
                         note = transmembrane domain, CD8tm2
source                   1..23
                         mol_type = protein
                         organism = synthetic construct
SEQUENCE: 18
IYIWAPLAGT CGVLLLSLVI TLY                                        23

SEQ ID NO: 19            moltype = AA  length = 24
FEATURE                  Location/Qualifiers
REGION                   1..24
                         note = transmembrane domain, CD8tm3
source                   1..24
                         mol_type = protein
                         organism = synthetic construct
SEQUENCE: 19
IYIWAPLAGT CGVLLLSLVI TLYC                                       24

SEQ ID NO: 20            moltype = AA  length = 27
FEATURE                  Location/Qualifiers
REGION                   1..27
                         note = transmembrane domain, 41BB
source                   1..27
                         mol_type = protein
                         organism = synthetic construct
SEQUENCE: 20
IISFFLALTS TALLFLLFFL TLRFSVV                                    27

SEQ ID NO: 21            moltype = AA  length = 112
FEATURE                  Location/Qualifiers
source                   1..112
                         mol_type = protein
                         organism = Homo sapiens
SEQUENCE: 21
```

-continued

```
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 22            moltype = AA   length = 41
FEATURE                  Location/Qualifiers
source                   1..41
                         mol_type = protein
                         organism = Homo sapiens
SEQUENCE: 22
RSKRSRLLHS DYMNMTPRRP GPTRKHYQPY APPRDFAAYR S                       41

SEQ ID NO: 23            moltype = AA   length = 41
FEATURE                  Location/Qualifiers
source                   1..41
                         mol_type = protein
                         organism = Homo sapiens
SEQUENCE: 23
RSKRSRGGHS DYMNMTPRRP GPTRKHYQPY APPRDFAAYR S                       41

SEQ ID NO: 24            moltype = AA   length = 42
FEATURE                  Location/Qualifiers
source                   1..42
                         mol_type = protein
                         organism = Homo sapiens
SEQUENCE: 24
KRGRKKLLYI FKQPFMRPVQ TTQEEDGCSC RFPEEEEGGC EL                      42

SEQ ID NO: 25            moltype = AA   length = 42
FEATURE                  Location/Qualifiers
source                   1..42
                         mol_type = protein
                         organism = Homo sapiens
SEQUENCE: 25
ALYLLRRDQR LPPDAHKPPG GGSFRTPIQE EQADAHSTLA KI                      42

SEQ ID NO: 26            moltype = AA   length = 566
FEATURE                  Location/Qualifiers
REGION                   1..566
                         note = chimeric protein sequence, Figure 18
source                   1..566
                         mol_type = protein
                         organism = synthetic construct
SEQUENCE: 26
MLLLVTSLLL CELPHPAFLL IPDIQLTQSP STLSASVGDR VTITCSASSS VRFIHWYQQK   60
PGKAPKRLIY DTSKLASGVP SRFSGSGSGT DFTLTISSLQ PEDFATYYCQ QWGSSPFTFG  120
QGTKVEIKGS TSGGGSGGGS GGGGSSEVQL VEYGGGLVQP GGSLRLSCAA SGFNIKDYYI  180
HWVRQAPGKG LEWVAWIDPE NGDTEFVPKF QGRATMSADT SKNTAYLQMN SLRAEDTAVY  240
YCKTGGFWGQ GTLVTVSSES KYGPPCPPCP GGGSSGGGSG GQPREPQVYT LPPSQEEMTK  300
NQVSLTCLVK GFYPSDIAVE WESNGQPENN YKTTPPVLDS DGSFFLYSRL TVDKSRWQEG  360
NVFSCSVMHE ALHNHYTQKS LSLSLGKMAL IVLGGVAGLL LFIGLGIFFK RGRKKLLYIF  420
KQPFMRPVQT TQEEDGCSCR FPEEEEGGCE LGGGRVKFSR SADAPAYQQG QNQLYNELNL  480
GRREEYDVLD KRRGRDPEMG GKPRRKNPQE GLYNELQKDK MAEAYSEIGM KGERRRGKGH  540
DGLYQGLSTA TKDTYDALHM QALPPR                                       566

SEQ ID NO: 27            moltype = AA   length = 671
FEATURE                  Location/Qualifiers
REGION                   1..671
                         note = chimeric protein
                          PSCAscFv-IgG4(EQ)-CD28tm-CD28gg-zeta, Figure 19
source                   1..671
                         mol_type = protein
                         organism = synthetic construct
SEQUENCE: 27
MLLLVTSLLL CELPHPAFLL IPDIQLTQSP STLSASVGDR VTITCSASSS VRFIHWYQQK   60
PGKAPKRLIY DTSKLASGVP SRFSGSGSGT DFTLTISSLQ PEDFATYYCQ QWGSSPFTFG  120
QGTKVEIKGS TSGGGSGGGS GGGGSSEVQL VEYGGGLVQP GGSLRLSCAA SGFNIKDYYI  180
HWVRQAPGKG LEWVAWIDPE NGDTEFVPKF QGRATMSADT SKNTAYLQMN SLRAEDTAVY  240
YCKTGGFWGQ GTLVTVSSES KYGPPCPPCP APEFEGGPSV FLFPPKPKDT LMISRTPEVT  300
CVVVDVSQED PEVQFNWYVD GVEVHNAKTK PREEQFQSTY RVVSVLTVLH QDWLNGKEYK  360
CKVSNKGLPS SIEKTISKAK GQPREPQVYT LPPSQEEMTK NQVSLTCLVK GFYPSDIAVE  420
WESNGQPENN YKTTPPVLDS DGSFFLYSRL TVDKSRWQEG NVFSCSVMHE ALHNHYTQKS  480
LSLSLGKMFW VLVVVGGVLA CYSLLVTVAF IIFWVRSKRS RGGHSDYMNM TPRRPGPTRK  540
HYQPYAPPRD FAAYRSGGGR VKFSRSADAP AYQQGQNQLY NELNLGRREE YDVLDKRRGR  600
DPEMGGKPRR KNPQEGLYNE LQKDKMAEAY SEIGMKGERR RGKGHDGLYQ GLSTATKDTY  660
DALHMQALPP R                                                       671

SEQ ID NO: 28            moltype = AA   length = 447
FEATURE                  Location/Qualifiers
REGION                   1..447
```

-continued

```
                          note = chimeric protein sequence, Figure 20
source                    1..447
                          mol_type = protein
                          organism = synthetic construct
SEQUENCE: 28
MLLLVTSLLL CELPHPAFLL IPDIQLTQSP STLSASVGDR VTITCSASSS VRFIHWYQQK   60
PGKAPKRLIY DTSKLASGVP SRFSGSGSGT DFTLTISSLQ PEDFATYYCQ QWGSSPFTFG  120
QGTKVEIKGS TSGGGSGGGS GGGGSSEVQL VEYGGGLVQP GGSLRLSCAA SGFNIKDYYI  180
HWVRQAPGKG LEWVAWIDPE NGDTEFVPKF QGRATMSADT SKNTAYLQMN SLRAEDTAVY  240
YCKTGGFWGQ GTLVTVSSGG GSSGGGSGMA LIVLGGVAGL LLFIGLGIFF KRGRKKLLYI  300
FKQPFMRPVQ TTQEEDGCSC RFPEEEEGGC ELGGGRVKFS RSADAPAYQQ GQNQLYNELN  360
LGRREEYDVL DKRRGRDPEM GGKPRRKNPQ EGLYNELQKD KMAEAYSEIG MKGERRRGKG  420
HDGLYQGLST ATKDTYDALH MQALPPR                                     447

SEQ ID NO: 29          moltype = AA   length = 571
FEATURE                Location/Qualifiers
REGION                 1..571
                       note = chimeric protein sequence, Figure 21
source                 1..571
                       mol_type = protein
                       organism = synthetic construct
SEQUENCE: 29
MLLLVTSLLL CELPHPAFLL IPDIQLTQSP STLSASVGDR VTITCSASSS VRFIHWYQQK   60
PGKAPKRLIY DTSKLASGVP SRFSGSGSGT DFTLTISSLQ PEDFATYYCQ QWGSSPFTFG  120
QGTKVEIKGS TSGGGSGGGS GGGGSSEVQL VEYGGGLVQP GGSLRLSCAA SGFNIKDYYI  180
HWVRQAPGKG LEWVAWIDPE NGDTEFVPKF QGRATMSADT SKNTAYLQMN SLRAEDTAVY  240
YCKTGGFWGQ GTLVTVSSES KYGPPCPPCP GGGSSGGGSG GQPREPQVYT LPPSQEEMTK  300
NQVSLTCLVK GFYPSDIAVE WESNGQPENN YKTTPPVLDS DGSFFLYSRL TVDKSRWQEG  360
NVFSCSVMHE ALHNHYTQKS LSLSLGKMFW VLVVVGGVLA CYSLLVTVAF IIFWVRSKRS  420
RGGHSDYMNM TPRRPGPTRK HYQPYAPPRD FAAYRSGGGR VKFSRSADAP AYQQGQNQLY  480
NELNLGRREE YDVLDKRRGR DPEMGGKPRR KNPQEGLYNE LQKDKMAEAY SEIGMKGERR  540
RGKGHDGLYQ GLSTATKDTY DALHMQALPP R                                571

SEQ ID NO: 30          moltype = AA   length = 666
FEATURE                Location/Qualifiers
REGION                 1..666
                       note = chimeric protein PSCAscFv-IgG4(EQ)-CD4tm-4IBB-zeta,
                        Figure 22
source                 1..666
                       mol_type = protein
                       organism = synthetic construct
SEQUENCE: 30
MLLLVTSLLL CELPHPAFLL IPDIQLTQSP STLSASVGDR VTITCSASSS VRFIHWYQQK   60
PGKAPKRLIY DTSKLASGVP SRFSGSGSGT DFTLTISSLQ PEDFATYYCQ QWGSSPFTFG  120
QGTKVEIKGS TSGGGSGGGS GGGGSSEVQL VEYGGGLVQP GGSLRLSCAA SGFNIKDYYI  180
HWVRQAPGKG LEWVAWIDPE NGDTEFVPKF QGRATMSADT SKNTAYLQMN SLRAEDTAVY  240
YCKTGGFWGQ GTLVTVSSES KYGPPCPPCP APEFEGGPSV FLFPPKPKDT LMISRTPEVT  300
CVVVDVSQED PEVQFNWYVD GVEVHNAKTK PREEQFQSTY RVVSVLTVLH QDWLNGKEYK  360
CKVSNKGLPS SIEKTISKAK GQPREPQVYT LPPSQEEMTK NQVSLTCLVK GFYPSDIAVE  420
WESNGQPENN YKTTPPVLDS DGSFFLYSRL TVDKSRWQEG NVFSCSVMHE ALHNHYTQKS  480
LSLSLGKMAL IVLGGVAGLL LFIGLGIFFK RGRKKLLYIF KQPFMRPVQT TQEEDGCSCR  540
FPEEEEGGCE LGGGRVKFSR SADAPAYQQG QNQLYNELNL GRREEYDVLD KRRGRDPEMG  600
GKPRRKNPQE GLYNELQKDK MAEAYSEIGM KGERRRGKGH DGLYQGLSTA TKDTYDALHM  660
QALPPR                                                           666

SEQ ID NO: 31          moltype = AA   length = 452
FEATURE                Location/Qualifiers
REGION                 1..452
                       note = chimeric protein PSCAscFv-L-CD28tm-4IBB-zeta, Figure
                        23
source                 1..452
                       mol_type = protein
                       organism = synthetic construct
SEQUENCE: 31
MLLLVTSLLL CELPHPAFLL IPDIQLTQSP STLSASVGDR VTITCSASSS VRFIHWYQQK   60
PGKAPKRLIY DTSKLASGVP SRFSGSGSGT DFTLTISSLQ PEDFATYYCQ QWGSSPFTFG  120
QGTKVEIKGS TSGGGSGGGS GGGGSSEVQL VEYGGGLVQP GGSLRLSCAA SGFNIKDYYI  180
HWVRQAPGKG LEWVAWIDPE NGDTEFVPKF QGRATMSADT SKNTAYLQMN SLRAEDTAVY  240
YCKTGGFWGQ GTLVTVSSGG GSSGGGSGMF WVLVVVGGVL ACYSLLVTVA FIIFWVRSKR  300
SRGGHSDYMN MTPRRPGPTR KHYQPYAPPR DFAAYRSGGG RVKFSRSADA PAYQQGQNQL  360
YNELNLGRRE EYDVLDKRRG RDPEMGGKPR RKNPQEGLYN ELQKDKMAEA YSEIGMKGER  420
RRGKGHDGLY QGLSTATKDT YDALHMQALP PR                               452

SEQ ID NO: 32          moltype = AA   length = 544
FEATURE                Location/Qualifiers
REGION                 1..544
                       note = chimeric protein sequence, Figure 18 without signal
source                 1..544
                       mol_type = protein
```

```
                        organism = synthetic construct
SEQUENCE: 32
DIQLTQSPST LSASVGDRVT ITCSASSSVR FIHWYQQKPG KAPKRLIYDT SKLASGVPSR   60
FSGSGSGTDF TLTISSLQPE DFATYYCQQW GSSPFTFGQG TKVEIKGSTS GGGSGGGSGG  120
GGSSEVQLVE YGGGLVQPGG SLRLSCAASG FNIKDYYIHW VRQAPGKGLE WVAWIDPENG  180
DTEFVPKFQG RATMSADTSK NTAYLQMNSL RAEDTAVYYC KTGGFWGQGT LVTVSSESKY  240
GPPCPPPCPGG GSSGGGSGGQ PREPQVYTLP PSQEEMTKNQ VSLTCLVKGF YPSDIAVEWE  300
SNGQPENNYK TTPPVLDSDG SFFLYSRLTV DKSRWQEGNV FSCSVMHEAL HNHYTQKSLS  360
LSLGKMALIV LGGVAGLLLF IGLGIFFKRG RKKLLYIFKQ PFMRPVQTTQ EEDGCSCRFP  420
EEEEGGCELG GGRVKFSRSA DAPAYQQGQN QLYNELNLGR REEYDVLDKR RGRDPEMGGK  480
PRRKNPQEGL YNELQKDKMA EAYSEIGMKG ERRRGKGHDG LYQGLSTATK DTYDALHMQA  540
LPPR                                                              544

SEQ ID NO: 33          moltype = AA  length = 649
FEATURE                Location/Qualifiers
REGION                 1..649
                       note = chimeric protein
                        PSCAscFv-IgG4(EQ)-CD28tm-CD28gg-zeta, Figure 19without
                        signal
source                 1..649
                       mol_type = protein
                       organism = synthetic construct
SEQUENCE: 33
DIQLTQSPST LSASVGDRVT ITCSASSSVR FIHWYQQKPG KAPKRLIYDT SKLASGVPSR   60
FSGSGSGTDF TLTISSLQPE DFATYYCQQW GSSPFTFGQG TKVEIKGSTS GGGSGGGSGG  120
GGSSEVQLVE YGGGLVQPGG SLRLSCAASG FNIKDYYIHW VRQAPGKGLE WVAWIDPENG  180
DTEFVPKFQG RATMSADTSK NTAYLQMNSL RAEDTAVYYC KTGGFWGQGT LVTVSSESKY  240
GPPCPPPCPAP EFEGGPSVFL FPPKPKDTLM ISRTPEVTCV VVDVSQEDPE VQFNWYVDGV  300
EVHNAKTKPR EEQFQSTYRV VSVLTVLHQD WLNGKEYKCK VSNKGLPSSI EKTISKAKGQ  360
PREPQVYTLP PSQEEMTKNQ VSLTCLVKGF YPSDIAVEWE SNGQPENNYK TTPPVLDSDG  420
SFFLYSRLTV DKSRWQEGNV FSCSVMHEAL HNHYTQKSLS LSLGKMFWVL VVVGGVLACY  480
SLLVTVAFII FWVRSKRSRG GHSDYMNMTP RRPGPTRKHY QPYAPPRDFA AYRSGGGRVK  540
FSRSADAPAY QQGQNQLYNE LNLGRREEYD VLDKRRGRDP EMGGKPRRKN PQEGLYNELQ  600
KDKMAEAYSE IGMKGERRRG KGHDGLYQGL STATKDTYDA LHMQALPPR             649

SEQ ID NO: 34          moltype = AA  length = 447
FEATURE                Location/Qualifiers
REGION                 1..447
                       note = chimeric protein sequence, Figure 20 without signal
source                 1..447
                       mol_type = protein
                       organism = synthetic construct
SEQUENCE: 34
MLLLVTSLLL CELPHPAFLL IPDIQLTQSP STLSASVGDR VTITCSASSS VRFIHWYQQK   60
PGKAPKRLIY DTSKLASGVP SRFSGSGSGT DFTLTISSLQ PEDFATYYCQ QWGSSPFTFG  120
QGTKVEIKGS TSGGGSGGGS GGGGSSEVQL VEYGGGLVQP GGSLRLSCAA SGFNIKDYYI  180
HWVRQAPGKG LEWVAWIDPE NGDTEFVPKF QGRATMSADT SKNTAYLQMN SLRAEDTAVY  240
YCKTGGFWGQ GTLVTVSSGG GSSGGGSGMA LIVLGGVAGL LLFIGLGIFF KRGRKKLLYI  300
FKQPFMRPVQ TTQEEDGCSC RFPEEEEGGC ELGGGRVKFS RSADAPAYQQ GQNQLYNELN  360
LGRREEYDVL DKRRGRDPEM GGKPRRKNPQ EGLYNELQKD KMAEAYSEIG MKGERRRGKG  420
HDGLYQGLST ATKDTYDALH MQALPPR                                     447

SEQ ID NO: 35          moltype = AA  length = 549
FEATURE                Location/Qualifiers
REGION                 1..549
                       note = chimeric protein sequence, Figure 21 without signal
source                 1..549
                       mol_type = protein
                       organism = synthetic construct
SEQUENCE: 35
DIQLTQSPST LSASVGDRVT ITCSASSSVR FIHWYQQKPG KAPKRLIYDT SKLASGVPSR   60
FSGSGSGTDF TLTISSLQPE DFATYYCQQW GSSPFTFGQG TKVEIKGSTS GGGSGGGSGG  120
GGSSEVQLVE YGGGLVQPGG SLRLSCAASG FNIKDYYIHW VRQAPGKGLE WVAWIDPENG  180
DTEFVPKFQG RATMSADTSK NTAYLQMNSL RAEDTAVYYC KTGGFWGQGT LVTVSSESKY  240
GPPCPPPCPGG GSSGGGSGGQ PREPQVYTLP PSQEEMTKNQ VSLTCLVKGF YPSDIAVEWE  300
SNGQPENNYK TTPPVLDSDG SFFLYSRLTV DKSRWQEGNV FSCSVMHEAL HNHYTQKSLS  360
LSLGKMFWVL VVVGGVLACY SLLVTVAFII FWVRSKRSRG GHSDYMNMTP RRPGPTRKHY  420
QPYAPPRDFA AYRSGGGRVK FSRSADAPAY QQGQNQLYNE LNLGRREEYD VLDKRRGRDP  480
EMGGKPRRKN PQEGLYNELQ KDKMAEAYSE IGMKGERRRG KGHDGLYQGL STATKDTYDA  540
LHMQALPPR                                                         549

SEQ ID NO: 36          moltype = AA  length = 644
FEATURE                Location/Qualifiers
REGION                 1..644
                       note = chimeric protein PSCAscFv-IgG4(EQ)-CD4tm-4IBB-zeta,
                        Figure 22without signal
source                 1..644
                       mol_type = protein
                       organism = synthetic construct
```

```
SEQUENCE: 36
DIQLTQSPST LSASVGDRVT ITCSASSSVR FIHWYQQKPG KAPKRLIYDT SKLASGVPSR   60
FSGSGSGTDF TLTISSLQPE DFATYYCQQW GSSPFTFGQG TKVEIKGSTS GGGSGGGSGG  120
GGGSSEVQLVE YGGGLVQPGG SLRLSCAASG FNIKDYYIHW VRQAPGKGLE WVAWIDPENG  180
DTEFVPKFQG RATMSADTSK NTAYLQMNSL RAEDTAVYYC KTGGFWGQGT LVTVSSESKY  240
GPPCPPCPAP EFEGGPSVFL FPPKPKDTLM ISRTPEVTCV VVDVSQEDPE VQFNWYVDGV  300
EVHNAKTKPR EEQFQSTYRV VSVLTVLHQD WLNGKEYKCK VSNKGLPSSI EKTISKAKGQ  360
PREPQVYTLP PSQEEMTKNQ VSLTCLVKGF YPSDIAVEWE SNGQPENNYK TTPPVLDSDG  420
SFFLYSRLTV DKSRWQEGNV FSCSVMHEAL HNHYTQKSLS LSLGKMALIV LGGVAGLLLF  480
IGLGIFFKRG RKKLLYIFKQ PFMRPVQTTQ EEDGCSCRFP EEEEGGCELG GGRVKFSRSA  540
DAPAYQQGQN QLYNELNLGR REEYDVLDKR RGRDPEMGGK PRRKNPQEGL YNELQKDKMA  600
EAYSEIGMKG ERRRGKGHDG LYQGLSTATK DTYDALHMQA LPPR                   644

SEQ ID NO: 37              moltype = AA  length = 430
FEATURE                    Location/Qualifiers
REGION                     1..430
                           note = chimeric protein PSCAscFv-L-CD28tm-4IBB-zeta, Figure
                           23 withoutsignal
source                     1..430
                           mol_type = protein
                           organism = synthetic construct
SEQUENCE: 37
DIQLTQSPST LSASVGDRVT ITCSASSSVR FIHWYQQKPG KAPKRLIYDT SKLASGVPSR   60
FSGSGSGTDF TLTISSLQPE DFATYYCQQW GSSPFTFGQG TKVEIKGSTS GGGSGGGSGG  120
GGGSSEVQLVE YGGGLVQPGG SLRLSCAASG FNIKDYYIHW VRQAPGKGLE WVAWIDPENG  180
DTEFVPKFQG RATMSADTSK NTAYLQMNSL RAEDTAVYYC KTGGFWGQGT LVTVSSGGGS  240
SGGGSGMFWV LVVVGGVLAC YSLLVTVAFI IFWVRSKRSR GGHSDYMNMT PRRPGPTRKH  300
YQPYAPPRDF AAYRSGGGRV KFSRSADAPA YQQGQNQLYN ELNLGRREEY DVLDKRRGRD  360
PEMGGKPRRK NPQEGLYNEL QKDKMAEAYS EIGMKGERRR GKGHDGLYQG LSTATKDTYD  420
ALHMQALPPR                                                        430

SEQ ID NO: 38              moltype = AA  length = 236
FEATURE                    Location/Qualifiers
REGION                     1..236
                           note = an scFv directed against PSCA
source                     1..236
                           mol_type = protein
                           organism = synthetic construct
SEQUENCE: 38
DIQLTQSPST LSASVGDRVT ITCSASSSVR FIHWYQQKPG KAPKRLIYDT SKLASGVPSR   60
FSGSGSGTDF TLTISSLQPE DFATYYCQQW GSSPFTFGQG TKVEIKGSTS GGGSGGGSGG  120
GGGSSEVQLVE YGGGLVQPGG SLRLSCAASG FNIKDYYIHW VRQAPGKGLE WVAWIDPENG  180
DTEFVPKFQG RATMSADTSK NTAYLQMNSL RAEDTAVYYC KTGGFWGQGT LVTVSS      236
```